Figure 1A:
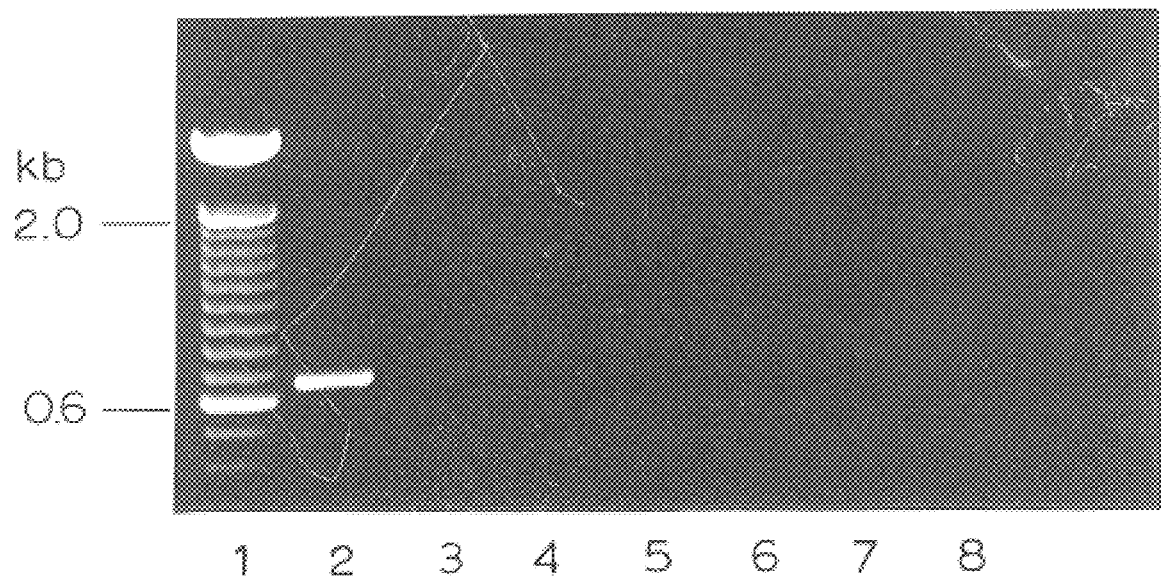

United States Patent [19]

Morgan et al.

[11] Patent Number: 6,054,275
[45] Date of Patent: Apr. 25, 2000

[54] DETECTION METHODS FOR CRYPTOSPORIDIUM

[75] Inventors: Una Morgan, Hamilton Hill; Richard Christopher Andrew Thompson, Roleystone, both of Australia

[73] Assignee: Murdoch University, Western Australia, Australia

[21] Appl. No.: 08/981,462

[22] PCT Filed: Jun. 25, 1996

[86] PCT No.: PCT/AU96/00387

§ 371 Date: Mar. 20, 1998

§ 102(e) Date: Mar. 20, 1998

[87] PCT Pub. No.: WO97/02281

PCT Pub. Date: Jan. 23, 1997

[30] Foreign Application Priority Data

Jun. 30, 1995 [AU] Australia ............................. PN 3916

[51] Int. Cl.[7] .................................................. C12Q 1/68
[52] U.S. Cl. ............................... 435/6; 435/29; 435/91.2; 435/34
[58] Field of Search ................................ 435/29, 91.2, 34, 435/6

[56] References Cited

U.S. PATENT DOCUMENTS 5,770,368 6/1998 De Leon et al. ........................... 435/6

*Primary Examiner*—Kenneth R. Horlick
*Assistant Examiner*—Janell E. Taylor
*Attorney, Agent, or Firm*—Marshall, O'Toole, Gerstein, Murray & Borun

[57] ABSTRACT

The invention provides a purified and isolated Cryptosporidium DNA sequence comprising the nucleotide sequence:

GATGGTACTGGATAGATAGTGGAAGTC-
CCGTATCAGTTCGAGATTCTGAAATTA ATTGGACAT-
CAAGTTATAAAGCAAGCTGGTTATTAA-
GATTCAAATTTCCCTTTGA
AAAGTGTGGCTTTTTTGATATTG-
GAGGGTTAGGAAGAAGGTT plus methods and kits for detecting and/or identifying the presence of Cryptosporidium.

15 Claims, 19 Drawing Sheets

FIGURE 6A

```
HUMAN 1   ------------------------------------------TATCAGTTCGAGATTCTGAA
HUMAN 2   ------------------GGATAGATAGTGGAAGTCCCGTATCAGTTCGAGATTCTGAA
CALF  1   GATGGGTACTGGGATAGATAGTGGAAGTCCCGTATCAGTTCGAGATTCTGAA
CALF  2   ------------------------------------------TATCAGTTCGAGATTCTGAA
                                                    ********************
```

FIGURE 6B

HUMAN 1  ATTAATTGGACATCAAGTTATAATGCAAGCTGGTTATTAAGATTCAAATT
HUMAN 2  ATTAATTGGACATCAAGTTATAATGCAAGCTGGTTATTAAGATTCAAATT
CALF 1   ATTAATTGGACATCAAGTTATAAAGCAAGCTGGTTATTAAGATTCAAATT
CALF 2   ATTAATTGGACATCAAGTTATAAAGCAAGCTGGTTATTAAGATTCAAATT
         ********************  *************************

FIGURE 6C

```
HUMAN 1  TCCTTTTGAAAAGTGTGGTTTTTTTGATATTGGAGGGGTTAGGAAGAAGGC
HUMAN 2  TCCTTTTGAAAAGTGTGGTTTTTTTGATATTGGAGGGGTTAGGAAGAAGGC
CALF  1  TCCCTTTGAAAAGTGTGGCTTTTTTGATATTGGAGGGGTTAGGAAGAAGGC
CALF  2  TCCCTTTGAAAAGTGTGGCTTTTTTGATATTGGAGGGGTTAGGAAGAAGGC
         *** ******************* **************************
```

FIGURE 6D

HUMAN 1  CGTGTTGGGCTTATAGATTCTGAGCTTTCTTGTGCAGTTTGTGGTACAGTA
HUMAN 2  CGTGTTGGGCTTATAGATTCTGAGCTTTCTTGTGCAGTTTGTGGTACAGTA
CALF 1   CGTGTTGGGCTTATAGATTCTGAGCTTTCTTGTGCAGTTTGTGGTACAGTA
CALF 2   CGTGTTGGGCTTATAGATTCTGAGCTTTCTTGTGCAGTTTGTGGTACAGTA
         **************************************************

FIGURE 6E

```
HUMAN 1  GCTTATGATTCTGGTGGACTGAATCCCAATAAATATTCAGAGCTAATTAA
HUMAN 2  GCTTATGATTCTGGTGGACTGAATCCCAATAAATATTCAGAGCTAATTAA
CALF  1  GCTTATGATTCTGGTGGGCTGAATCCCAATAAATATTCAGAGCTAATTAA
CALF  2  GCTTATGATTCTGGTGGGCTGAATCCCAATAAATATTCAGAGCTAATTAA
         ***************** ************************** *****
```

FIGURE 6F

HUMAN 1  GCAGACTGATGAAATTATTAGTAAAGAGCCAAAGCTTGATTTTCCAGGCT
HUMAN 2  GCAGACTGATGAAATTATTAGTAAAGAGCCAAAGCTTGATTTTCCAGGCT
CALF  1  GCAGACTGATGAAATTATTAGTAAAGAGCCAAAGCTTGATCTTCCAGGTT
CALF  2  GCAGACTGATGAAATTATTAGTAAAGAGCCAAAGCTTGATCTTCCAGGTT
         ************************************ **** *

FIGURE 6G

HUMAN 1  ACAATAATTTGAACTGTACAGATGCTTGGGAGAATAATTTATCAGTCGGT
HUMAN 2  ACAATAATTTGAACTGTACAGATGCTTGGGAGAATAATTTATCAGTCGGT
CALF 1   ACAATAATTTGAACTGTACAGATGCTTGGGAGAATAATTTATCAGTTGGT
CALF 2   ACAATAATTTGAACTGTACAGATGCTTGGGAGAATAATTTATCAGTTGGT
         ********************************************:*

FIGURE 6H

```
HUMAN 1  CTTTGTCAAAAATGTTTCAAATATCCTGGACTCAGCTTGGAGCTCATATCA
HUMAN 2  CTTTGTCAAAAATGTTTCAAATATCCTGGACTCAGCTTGGAGCTCATATCA
CALF  1  CTTTGTCAAAAATGTCTCAAATATCCTGGACTCAGCTTGGAGCTCGTATCA
CALF  2  CTTTGTCAAAAATGTCTCAAATATCCTGGACTCAGCTTGGAGCTCGTATCA
         *************** ******************************* ****
```

FIGURE 6I

HUMAN 1  GAGTTCGTTAAACTTTCCTAGCATCAACTTTAATTGGAAAGAGGATTCAA
HUMAN 2  GAGTTCGTTAAACTTTCCTAGCATCAACTTTAATTGGAAAGAGGATTCAA
CALF 1   GAGTTCGTTAAACTTTCCTAGTATCAACTTTAACTGGAAAGAGGATTCAA
CALF 2   GAGTTCGTTAAACTTTCCTAGTATCAACTTTAACTGGAAAGAGGATTCAA
         ****************** ******** **************

FIGURE 6J

```
HUMAN 1  CTAACGAAGGAGGGGACCAAGTTTACCATAATTCTTATTTGGATCTTCCA
HUMAN 2  CTAACGAAGGAGGGGACCAAGTTTACCATAATTCTTATTTGGATCTTCCA
CALF 1   CTAACGAAGGAGGGGACCAAGTTTACCATAATTCTTATTTGGATCTTCCA
CALF 2   CTAACGAAGGAGGGGACCAAGTTTACCATAATTCTTATTTGGATCTTCCA
         **************************************************
```

FIGURE 6K

HUMAN 1  AGGTATAAGCAGAGAAGAAAACATTTTATTGGGATCAGGATCCAGGTACTAT
HUMAN 2  AGGTATAAGCAGAGAAGAAAACATTTTATTGGGATCAGGATCCAGGTACTAT
CALF 1   AGGTATAAGCAGAGAAGAAAACATTTTATTGGGATCAGGATCCAGGTACTAT
CALF 2   AGGTATAAGCAGAGAAGAAAACATTTTATTGGGATCAGGATCCAGGTACTAT
         ****************************************************

FIGURE 6L

Human 1  TCCAGCTTTGTCTCTGATGAAATGAAGCTCATTGGTTTAAGCGCTCAACCAA
Human 2  TCCAGCTTTGTCTCTGATGAAATGAAGCTCATTGGTTTAAGCGCTCAACCAA
Calf 1   TCCAGCTTTGTCTCTGATGAAATGAAGCTCATTGGTTTAAGCGCTCAACCAA
Calf 2   TCCAGCTTTGTCTCTGATGAAATGAAGCTCATTGGTTTAAGCGCTCAACCAA
         ****************************************************

FIGURE 6M

```
HUMAN 1  CATACCATCCTTTGGCTAGAAGCTCATCTGGAA---------------
HUMAN 2  CATACCATCCTTTGGCTAGAAGCTCATCTGGAAGTCTGA---------
CALF  1  CATACCATCCTTTGGGATAGAAGCTCATCTGGAAGTTTTGAGTCTGATAGT----
CALF  2  CATACCATCCTTTGGGATAGAAGCTCATCTGGAAGTTTTG--------
         *************** ****************
```

FIGURE 6N

HUMAN 1 ------------
HUMAN 2 ------------
CALF 1  ACAGAATCCGGGGCGTGCGAATGAAGAAAGAAACGATAC
CALF 2  ------------

DETECTION METHODS FOR CRYPTOSPORIDIUM

The present invention relates to a method for detecting microorganisms of the genus Cryptosporidium and more particularly *Cryptosporidium parvum*.

The protozoan parasite *Cryptosporidium parvum* is recognised as an important cause of diarrhoeal illness primarily in infants and young children, (although immunologically healthy adults are susceptible) and is associated with persistent diarrhoea and severe illness in malnourished children. It is also a serious opportunistic pathogen in immunocompromised individuals, causing severe and unremitting diarrhoea that is often intractable to therapy. Chronic cryptosporidiosis is reported in as many as 10% of persons with AIDS in the United States and there are currently no effective therapeutic strategies for treating Cryptosporidium infection.

Waterborne transmission of this enteric parasite is a major concern. The infective stage (oocyst) of Cryptosporidium is transmitted by the faecal-oral route, with infected individuals excreting Cryptosporidium oocysts. Animals as well as humans may serve as sources of environmental contamination and human infection. The oocyst is environmentally stable and is able to survive and penetrate routine wastewater treatment and is resistant to inactivation by drinking water disinfectants. There are several species of Cryptosporidium but *Cryptosporidium parvum* is believed to cause the majority of mammalian infections. *Cryptosporidium parvum* oocysts are resistant to chlorination procedures normally used for water treatment, and contamination of water supplies can cause massive outbreaks of the disease such as the 1994 outbreak of cryptosporidiosis in Milwaukee resulting in diarrhoeal illness in an estimated 403,000 people.

In the absence of effective drugs to treat this ubiquitous infection, the control and clinical management of cryptosporidiosis depends upon rapid, accurate and sensitive diagnosis of the presence of the parasite, both in clinical specimens and environmental samples.

Clinical diagnosis of Cryptosporidium is time consuming, insensitive and generally requires the skills of highly trained operators. It has recently been reported that the detection limits of conventional diagnostic techniques for Cryptosporidium were as low as 50,000 oocysts per gram of faeces and that mean oocyst losses ranged from 51.2% to 99.6%. Further, the most commonly used coprodiagnostic techniques may fail to detect cryptosporidiosis in many immunocompromised and immunocompetent individuals. Immunological-based detection methods using immunofluorescence assays, enzyme-linked-immunosorbent and immunofluorescent-based diagnostic tests have been developed, several of which are now commercially available. Enzyme-linked immunoassays, although quick and easy to perform, generally show low sensitivity ranging from $3 \times 10^5$ to $1 \times 10^3$ oocysts per gram of faeces and monoclonal antibodies have the ability to bind to other microorganisms, i.e., to stain nonspecifically. In addition, Cryptosporidium isolates have been shown to exhibit a great deal of antigenic variability and therefore diagnostic antibodies may not recognise all isolates.

Environmental detection of Cryptosporidium generally involves filtering large volumes of water and examining it microscopically for Cryptosporidium oocysts by various staining or immunolabelling techniques. However, the efficiency of oocyst recovery may be as low as 1.3 to 5.5%. Recently, an alternative means of harvesting oocysts by calcium carbonate flocculation has been described with improved recovery ranging from 68% to >80%. Specialised flow cytometry and cell sorting techniques have also been developed to detect oocysts in water samples with greater sensitivity than conventional fluorescence microscopy. Although these methods are significantly more sensitive and considerably faster than conventional methods, they are costly and still require the skills of highly trained technical operators.

The development of the polymerase chain reaction (PCR) has permitted specific and sensitive detection of pathogens for clinical diagnosis and environmental monitoring. Diagnostic PCR primers have been described for the detection of Cryptosporidium. However, these primers suffer from a lack of sensitivity and are only able to detect at best approximately 200 Cryptosporidium oocysts reliably under optimum conditions. Further, most of the primers selected to date have only been tested on a small number of Cryptosporidium isolates and none of them have been tested directly on faeces. Thus, there exists a need for a sensitive detection method which is capable of identifying the presence of Cryptosporidium in faeces and environmental samples.

Given the severity and untreatable nature of Cryptosporidium infection in persons with AIDS, early detection of cryptosporidial infection in HIV-infected or AIDS patients who may be shedding low numbers of oocysts becomes increasingly important. A rapid, sensitive assay requiring little or no expertise on the part of the operator would be of great benefit in the early detection of asymptomatic or mild cryptosporidial infection in AIDS patients. It would improve clinical management of the disease with the option of initiating chemotherapy before the onset of symptoms, which may result in fewer cases progressing to severe, and often chronic, infections of this parasite.

The present invention provides nucleotide sequences which may be utilised in diagnostic assays to analyse samples for environmental contamination by Cryptosporidium oocysts and for the diagnosis of Cryptosporidium infections in patients.

Thus, the invention consists of a purified and isolated Cryptosporidium DNA sequence comprising the nucleotide sequence:

```
GATGGTACTGGATAGATAGTGGAAGTCCCGTATCAGTTCGAGATTCTGAAA
TTAATTGGACATCAAGTTATAAAGCAAGCTGGTTATTAAGATTCAAATTTC
CCTTTGAAAAGTGTGGCTTTTTTGATATTGGAGGGTTAGGAAGAAGGCCGT
GTTGGCTTATAGATTCTGAGCTTTCTTGTGCAGTTTGTGGTACAGTAGCTT
ATGATTCTGGTGGGCTGAATCCCAATAAATATTCAGAGCTAATTAAGCAGA
CTGATGAAATTATTAGTAAAGAGCCAAAGCTTGATCTTCCAGGTTACAATA
ATTTGAACTGTACAGATGCTTGGGAGAATAATTTATCAGTTGGTCTTTGTC
AAAATGTCTCAAATATCCTGGACTCAGCTTGGAGCTCGTATCAGAGTTCGT
TAAACTTTCCTAGTATCAACTTTAACTGGAAAGAGGATTCAACTAACGAAG
GAGGGGACCAAGTTTACCATAATTCTTATTTGGATCTTCCAAGGTATAAGC
AGAAGAAAACATTTTATTGGGATCAGGATCCAGGTACTATTCCAGCTTTGT
CTGATGAAATGAAGCTCATTGGTTTAAGCGCTCAACCAACATACCATCCTT
TGGATAGAAGCTCATCTGGAAGTTTTGAGTCTGATAGTACAGAATCCGGGC
GTGCGAATGAAGAAAGAAACGATAC
```

Preferably, the present invention consists of a method for detecting and/or identifying the presence of Cryptosporidium genomic material in a sample, said method comprising the steps of: selecting at least a primer or probe derived from the above mentioned nucleotide sequence; and then using that primer or probe to detect and/or identify the presence of Cryptosporidium genomic material.

From the above nucleotide sequence, oligonucleotides can be prepared which hybridise with the Cryptosporidium genome. The oligonucleotides may be used either as a primer(s) or as a probe(s) to detect the Cryptosporidium genome. Preferably, the primer(s) or probe(s) are specific for microorganisms of the species *Cryptosporidium parvum*.

The primer(s) or probe(s) for Cryptosporidium are preferably of a length which allows for the specific detection of such microorganisms. Primer(s) or probe(s) which are 5 to 8 nucleotides in length should be suitable for detecting the Cryptosporidium genome. Preferably, sequences of 10 to 50 nucleotides may be used as primer(s) or probe(s). More particularly, sequences of about 15 to 25 nucleotides may be used in the identification protocols, and about 20 to 24 nucleotides appear optimal.

Primer(s) or probe(s) can be selected and prepared using routine methods, including automated oligonucleotide synthetic methods. A complement to any unique portion of the above nucleotide sequence may be used as a primer(s) or probe(s) provided that it specifically binds o the Cryptosporidium genome. When used as primer(s) or probe(s) complete complementarity is desirable, though it may be unnecessary as the length of the fragment is increased. Among useful primer(s) or probe(s) for setecting and/or identifying Cryptosporidium isolates are, for example, the following sequences:

(i)      5' GGTACTGGATAGATAGTGGA 3'
(ii)     5' TCGCACGCCCGGATTCTGTA 3'
(iii)    5' AGTCCCGTATCAGTTCGAGA 3'
(iv)     5' ACTGGATAGATAGTGGAAGT 3'
(v)      5' TTTCTTTCTTCATTCGCACG 3'
(vi)     5' GTGGAAGTCCCGTATCAGTC 3'
(vii)    5' ACGCCCGGATTCTGTACTAT 3'
(viii)   5' GATAGATAGTGGAAGTCCCG 3'
(ix)     5' ACGCCCGGATTCTGTACTAT 3'
(x)      5' CTGAAATTAATTGGACATCA 3'
(xi)     5' GTACTATCAGACTCAAAACT 3'
(xii)    5' GTGGTACTGGATAGATAGTG 3'
(xiii)   5' GTATCGTTTCTTTCTTCATT 3'
(xiv)    5' TGGTACTGGATAGATAGTGG 3'
(xv)     5' TATCGTTTCTTTCTTCATTC 3'
(xvi)    5' TAGATAGTGGAAGTCCCGTA 3'
(xvii)   5' TCTTCATTCGCACGCCCGGA 3'
(xviii)  5' ATAGTGGAAGTCCCGTATCA 3'
(xix)    5' TTTCTTCATTCGCACGCCCG 3'
(xx)     5' CTGGATAGATAGTGGAAGTC 3'
(xxi)    5' CGTTTCTTTCTTCATTCGCA 3'
(xxii)   5' TAATTGGACATCAAGTATAA 3'
(xxiii)  5' GTACTATCAGACTCAAAACT 3'
(xxiv)   5' TCTGAAATTAATTGGACATC 3'
(xxv)    5' CTTCCAGATGAGCTTCTATC 3'
(xxvi)   5' GGTGGTACTGGATAGATAGT 3'
(xxvii)  5' GGTATCGTTTCTTTCTTCAT 3'
(xxviii) 5' GAGATTCTGAAATTAATTGG 3'
(xxix)   5' GTTGGCTTATAGATTCTGAGC 3'
(xxx)    5' GGTTATTAAGATTCAAATTTCC 3'
(xxxi)   5' TCCCGTATCAGTTCGAGATTCTG 3'
(xxxii)  5' CGAACTCTGATACGAGCTCCAAGC 3'
(xxxiii) 5' ATTCGAGATTCTGAAATTAATTGG 3'
(xxxiv)  5' GAATAGTACCTGGATCCTGATCCC 3'
(xxxv)   5' GATATTGGAGGGTTAGGAAGAAGG 3'
(xxxvi)  5' CTGTACAGTTCAAATTATTGTAACC 3'
(xxxvii) 5' GACTGATGAAATTATTAGTAAAGAGC 3'
(xxxviii) 5' CCTCCTTCGTTAGTTGAATCCTC 3'
(xxxix)  5' TCGCACGCCCGGATTCTGTA 3'
(xl)     5' CAGTTCAAATTATTGTAGCC 3'
(xli)    5' GTTCGAGATTCTGAAATTAATTGG 3'
(xlii)   5' GTCCCGTATCAGTTCGAGATTCTG 3'
(xliii)  5' GGAGGGTTAGGAAGAAGGCCGTG 3'
(xliv)   5' GCTTGGGAGAATAATTTATCAG 3'
(xlv)    5' GGGATCAGGATCCAGGTACTATTC 3'
(xlvi)   5' GTATCGTTTCTTTCTTCATTCGC 3'
(xlvii)  5' GGACCAAGTTTACCATAATTC 3'
(xlviii) 5' GGAGAATAATTTATCAGTTGGTC 3'
(xlix)   5' CAAGGTATAAGCAGAAGAAAAC 3'
(l)      5' CGCACGCCCGGATTCTGTACTATC 3'
(li)     5' ATGTCTCAAATATCCTGGACTCAG 3'
(lii)    5' GTACTGGATAGATAGTGGAAGTC 3'
(liii)   5' CACGGCCTTCTTCCTAACCCTCC 3'
(liv)    5' GGAAGTCCCGTATCAGTTCGAG 3'

Before the above probe(s) or primer(s) are used to detect and/or identify Cryptosporidium isolates in diagnostic methods such as those discussed herein, the sample to be analysed, such as a faecal sample, is preferably treated to extract the nucleic acid material contained therein. The resulting nucleic acid material from the sample may then be subjected to gel electrophoresis or other size separation techniques; the nucleic acid material may be blotted without size separation; alternatively, the sample may be tested without being subjected to such techniques. Whether size separation is employed in the identification protocol will depend on the type of assay being used. For example, size separation may be useful in hybridization assays.

Depending on the detection method which is employed to detect and/or identify the presence of Cryptosporidium isolates in a sample, the probe(s) or primer(s) may be labelled. Suitable labels and methods for labelling probes and primers are known in the art. For example, probes or primers may be labelled using radioactive deoxynucleotide labels incorporated by nick translation or end labelling, biotin labels, fluorescent labels or chemiluminescent labels may also be used. Alternatively, Cryptosporidium specific polynucleotides may be detected on agarose or poly acrylamide gels using, for example, ethidium bromide/UV visualisation or by silver staining techniques.

In one detection method, Cryptosporidium specific polynucleotides extracted from the sample may be treated with a labelled probe under hybridisation conditions of suitable stringencies. Usually high stringency conditions are desirable to prevent false positives. The stringency of hybridisation is determined by a number of factors during hybridisation and during the washing procedure, including temperature, ionic strength, length of time and concentration of reactants. A person of ordinary skill in the art would understand how these factors may be used together to modify the stringency of hybridisation.

Generally, it is expected that Cryptosporidium DNA will be present in samples from infected individuals and particularly in environmental samples at low concentrations. This level may dictate the need for amplification of the nucleic acids before they can be detected. Such amplification techniques are known in the art.

A method that is particularly preferred for detecting Cryptosporidium DNA is based on a PCR type test wherein a set of primers which are highly specific for Cryptosporidium DNA are used to amplify Cryptosporidium DNA present in a sample. The presence of the resultant product can then be detected using, for example, ethidium bromide/UV visualisation or by silver staining techniques. Alternatively, colourimetric detection of the PCR products using biotinylated primers could be employed to save time and to eliminate the need for agarose gel electrophoresis. Such an assay could also be modified to suit a 96 well microtitre format for bulk processing of samples.

Thus, in one embodiment the invention provides a method of detecting and/or identifying microorganisms of the genus Cryptosporidium comprising the steps of:

(i) selecting at least a set of primers from the above nucleotide sequence which are specific for Cryptosporidium DNA;

(ii) mixing the primers with a sample suspected of containing Cryptosporidium DNA;

(iii) amplifying any DNA to which the primers in step (ii) anneal by the polymerase chain reaction; and (iv) detecting the presence of the product of step (iii).

Although the above method has general application to one or more species of Cryptosporidium, preferably the primers which are selected in step (i) are highly specific for *Cryptosporidium parvum*.

Primer pairs which may be suitable for detecting *Cryptosporidium parvum* are preferably selected from the following sequences. In each primer set described the first mentioned primer represents the forward primer and the second mentioned primer represents the reverse primer.

(i)      5' ACTGGATAGATAGTGGAAGT 3'
         5' TTTCTTTCTTCATTCGCACG 3'
(ii)     5' GTGGAAGTCCCGTATCAGTC 3'
         5' ACGCCCGGATTCTGTACTAT 3'
(iii)    5' GATAGATAGTGGAAGTCCCG 3'
         5' ACGCCCGGATTCTGTACTAT 3'
(iv)     5' CTGAAATTAATTGGACATCA 3'
         5' GTACTATCAGACTCAAAACT 3'
(v)      5' GTGGTACTGGATAGATAGTG 3'
(vi)     5' GTATCGTTTCTTTCTTCATT 3'
         5' TGGTACTGGATAGATAGTGG 3'
         5' TATCGTTTCTTTCTTCATTC 3'
(vii)    5' TAGATAGTGGAAGTCCCGTA 3'
         5' TCTTCATTCGCACGCCCGGA 3'
(viii)   5' ATAGTGGAAGTCCCGTATCA 3'
         5' TTTCTTCATTCGCACGCCCG 3'
(ix)     5' CTGGATAGATAGTGGAAGTC 3'
         5' CGTTTCTTTCTTCATTCGCA 3'
(x)      5' TAATTGGACATCAAGTATAA 3'
         5' GTACTATCAGACTCAAAACT 3'
(xi)     5' TCTGAAATTAATTGGACATC 3'
         5' CTTCCAGATGAGCTTCTATC 3'
(xii)    5' GGTGGTACTGGATAGATAGT 3'
         5' GGTATCGTTTCTTTCTTCAT 3'
(xiii)   5' GGTACTGGATAGATAGTGGA 3'
         5' TCGCACGCCCGGATTCTGTA 3'
(xiv)    5' GAGATTCTGAAATTAATTGG 3'
         5' CCTCCTTCGTTAGTTGAATCC 3'
(xv)     5' GTTGGCTTATAGATTCTGAGC 3'
         5' CAGTTCAAATTATTGTAGCC 3'
(xvi)    5' GAGATTCTGAAATTAATTGG 3'
         5' CAGTTCAAATTATTGTAACC 3'
(xvii)   5' GTTGGCTTATAGATTCTGAGC 3'
         5' CCTCCTTCGTTAGTTGAATCC 3'
(xviii)  5' TAATTGGACATCAAGTTATAAAGC 3'
         5' GGAAGATCCAAATAAGAATTATGG 3'
(xix)    5' GGTTATTAAGATTCAAATTTCC 3'
         5' CGAACTCTGATACGAGCTCCAAGC 3'
(xx)     5' TCCCGTATCAGTTCGAGATTCTG 3'
         5' CGAACTCTGATACGAGCTCCAAGC 3'
(xxi)    5' GTTCGAGATTCTGAAATTAATTGG 3'
         5' CGAACTCTGATACGAGCTCCAAGC 3'
(xxii)   5' TAATTGGACATCAAGTTATAAAGC 3'
         5' CGAACTCTGATACGAGCTCCAAGC 3'
(xxiii)  5' GGTTATTAAGATTCAAATTTCC 3'
         5' CGAACTCTGATACGAGCTCCAAGC 3'
(xxiv)   5' TCCCGTATCAGTTCGAGATTCTG 3'
         5' GAATAGTACCTGGATCCTGATCCC 3'
(xxv)    5' TAATTGGACATCAAGTTATAAAGC 3'
         5' GAATAGTACCTGGATCCTGATCCC 3'

(xxvi)     5' GGTTATTAAGATTCAAATTTCC 3'
           5' GAATAGTACCTGGATCCTGATCCC 3'
(xxvii)    5' TCCCGTATCAGTTCGAGATTCTG 3'
           5' GGAAGATCCAAATAAGAATTATGG 3'
(xxviii)   5' GTTCGAGATTCTGAAATTAATTGG 3'
           5' GGAAGATCCAAATAAGAATTATGG 3'
(xxix)     5' GGTTATTAAGATTCAAATTTCC 3'
           5' GGAAGATCCAAATAAGAATTATGG 3'
(xxx)      5' ATTCGAGATTCTGAAATTAATTGG 3'
           5' GAATAGTACCTGGATCCTGATCCC 3'
(xxxi)     5' GATATTGGAGGGTTAGGAAGAAGG 3'
           5' CTGTACAGTTCAAATTATTGTAACC 3'
(xxxii)    5' GACTGATGAAATTATTAGTAAAGAGC 3'
           5' CCTCCTTCGTTAGTTGAATCCTC 3'
(xxxiii)   5' GGTACTGGATAGATAGTGGAAG 3'
           5' CCAGAATCATAAGCTACTGTACC 3'
(xxxiv)    5' GTCCCGTATCAGTTCGAGATTCTG 3'
           5' CCTCCTTCGTTAGTTGAATCCTC 3'
(xxxv)     5' GGGATCAGGATCCAGGTACTATTC 3'
           5' GTATCGTTTCTTTCTTCATTCGC 3'
(xxxvi)    5' GCTTGGGAGAATAATTTATCAG 3'
           5' CCTCCTTCGTTAGTTGAATCCTC 3'
(xxxvii)   5' GGACCAAGTTTACCATAATTC 3'
           5' GTATCGTTTCTTTCTTCATTCGC 3'
(xxxviii)  5' GGAGAATAATTTATCAGTTGGTC 3'
           5' GTATCGTTTCTTTCTTCATTCGC 3'
(xxxix)    5' CAAGGTATAAGCAGAAGAAAAC 3'
           5' CGCACGCCCGGATTCTGTACTATC 3'
(xl)       5' ATGTCTCAAATATCCTGGACTCAG 3'
           5' CGCACGCCCGGATTCTGTACTATC 3'
(xli)      5' GTACTGGATAGATAGTGGAAGTC 3'
           5' CACGGCCTTCTTCCTAACCCTCC 3'

Particularly preferred primer pairs that may be used in a diagnostic method for detecting *Cryptosporidium parvum* are desirably selected from the following primer sets. In each primer set described the first mentioned primer represents the forward primer and the second mentioned primer represents the reverse primer.

(i)        5' GGTACTGGATAGATAGTGGA 3'
           5' TCGCACGCCCGGATTCTGTA 3'
(ii)       5' GAGATTCTGAAATTAATTGG 3'
           5' CCTCCTTCGTTAGTTGAATCC 3'
(iii)      5' GTTGGCTTATAGATTCTGAGC 3'
           5' CAGTTCAAATTATTGTAGCC 3'
(iv)       5' GAGATTCTGAAATTAATTGG 3'
           5' CAGTTCAAATTATTGTAACC 3'
(v)        5' GTTGGCTTATAGATTCTGAGC 3'
           5' CCTCCTTCGTTAGTTGAATCC 3'
(vi)       5' TAATTGGACATCAAGTTATAAAGC 3'
           5' GGAAGATCCAAATAAGAATTATGG 3'
(vii)      5' GGTTATTAAGATTCAAATTTCC 3'
           5' CGAACTCTGATACGAGCTCCAAGC 3'
(viii)     5' TCCCGTATCAGTTCGAGATTCTG 3'
           5' CGAACTCTGATACGAGCTCCAAGC 3'
(ix)       5' GTTCGAGATTCTGAAATTAATTGG 3'
           5' CGAACTCTGATACGAGCTCCAAGC 3'
(x)        5' TAATTGGACATCAAGTTATAAAGC 3'
           5' CGAACTCTGATACGAGCTCCAAGC 3'
(xi)       5' GGTTATTAAGATTCAAATTTCC 3'
           5' CGAACTCTGATACGAGCTCCAAGC 3'
(xii)      5' TCCCGTATCAGTTCGAGATTCTG 3'
           5' GAATAGTACCTGGATCCTGATCCC 3'
(xiii)     5' TAATTGGACATCAAGTTATAAAGC 3'
           5' GAATAGTACCTGGATCCTGATCCC 3'
(xiv)      5' GGTTATTAAGATTCAAATTTCC 3'
           5' GAATAGTACCTGGATCCTGATCCC 3'
(xv)       5' TCCCGTATCAGTTCGAGATTCTG 3'
           5' GGAAGATCCAAATAAGAATTATGG 3'
(xvi)      5' GTTCGAGATTCTGAAATTAATTGG 3'
           5' GGAAGATCCAAATAAGAATTATGG 3'
(xvii)     5' GGTTATTAAGATTCAAATTTCC 3'
           5' GGAAGATCCAAATAAGAATTATGG 3'
(xviii)    5' ATTCGAGATTCTGAAATTAATTGG 3'
           5' GAATAGTACCTGGATCCTGATCCC 3'
(xix)      5' GATATTGGAGGGTTAGGAAGAAGG 3'
           5' CTGTACAGTTCAAATTATTGTAACC 3'
(xx)       5' GACTGATGAAATTATTAGTAAAGAGC 3'
           5' CCTCCTTCGTTAGTTGAATCCTC 3'
(xxi)      5' GGTACTGGATAGATAGTGGAAG 3'
           5' CCAGAATCATAAGCTACTGTACC 3'
(xxii)     5' GTCCCGTATCAGTTCGAGATTCTG 3'
           5' CCTCCTTCGTTAGTTGAATCCTC 3'

-continued (xxiii) 5' GGGATCAGGATCCAGGTACTATTC 3'

5' GTATCGTTTCTTTCTTCATTCGC 3'

(xxiv) 5' GCTTGGGAGAATAATTTATCAG 3'

5' CCTCCTTCGTTAGTTGAATCCTC 3'

(xxv) 5' GGACCAAGTTTACCATAATTC 3'

5' GTATCGTTTCTTTCTTCATTCGC 3'

(xxvi) 5' GGAGAATAATTTATCAGTTGGTC 3'

5' GTATCGTTTCTTTCTTCATTCGC 3'

(xxvii) 5' CAAGGTATAAGCAGAAGAAAAC 3'

5' CGCACGCCCGGATTCTGTACTATC 3'

(xxviii) 5' ATGTCTCAAATATCCTGGACTCAG 3'

5' CGCACGCCCGGATTCTGTACTATC 3'

(xxix) 5' GTACTGGATAGATAGTGGAAGTC 3'

5' CACGGCCTTCTTCCTAACCCTCC 3'

If for example the forward and reverse PCR primers are GGTACTGGATAGATAGTGGA and TCGCACGCCCG-GATTCTGTA respectively, a DNA fragment of approximately 668 nucleotides is produced upon amplification of *Cryptosporidium parvum* DNA. Alternatively, if the forward and reverse PCR primers are GAGATTCTGAAATTAAT-TGG and CCTCCTTCGTTAGTTGAATCC respectively, a DNA fragment of approximately 426 nucleotides is produced upon amplification of *Cryptosporidium parvum* DNA.

The methods described herein may be used to detect the presence or absence of Cryptosporidium DNA. However, they provide little information about the viability or infective potential of microorganisms within a sample. Thus, the detection method(s) described supra may be combined with one or more methods for testing Cryptosporidium viability. Such methods are widely known in the art. For example fluorogeneic vital-dye assays (eg. using propidium iodide) or the ability of Cryptosporidium to grow in vitro or in vivo may be used to determine the likely infectivity of virulence of the samples tested. Care should, however, be used when employing such methods. Current protocols for concentrating oocysts such as Percoll-sucrose gradients and sucrose density flotation may actually, selectively concentrate non-viable oocysts. Standard tests for viability such as fluorogeneic vital-dye assays may therefore be biased towards detection of non-viable oocysts. In addition, current protocols only sample a proportion of the total water body and the viability of cysts and oocysts not detected remains undetermined.

While the present invention relates to nucleotide sequences of Cryptosporidium and methods for detecting and/or identifying the presence of Cryptosporidium isolates, it will be appreciated that the sequences and method(s) may be made available in the form of a kit for the detection of Cryptosporidium isolates. Preferably, the kit provides a means for detecting *Cryptosporidium parvum* isolates.

Thus, in one embodiment of the invention there is provided a kit of detecting and/or identifying the presence of Cryptosporidium microorgansims is a sample, the kit comprising: at least a probe or set of primers which are specific for a region of the genome of Cryptosporidium, wherein the probe or primers are selected from the above mentioned nucleotide sequence.

Probes and primers can be packaged into diagnostic kits. Diagnostic kits may include the DNA probe or DNA primers which may be labelled; alternatively the probe or primers may be unlabelled and the ingredients for labelling the probe or amplifying the Cryptosporidium DNA using the primers may be included in the kit. The kit may also contain other suitably packaged reagents and materials needed for the particular detection protocols. The kit may also contain, for example, standards, as well as instructions for using the detection kits. Particular diagnostic kits may also contain the necessary reagents for conducting fluorogenic assays and/or for growing Cryptosporidium in cell culture.

The present invention will now be described by way of example only with reference to the following figures. It will be understood that all temperature ranges and other such variables prescribed in the examples are given as indicative only, and that parameters outside these limits may also provide useful results.

FIG. 1a represents an ethidium bromide stained 1% agarose gel showing specificity of the 021 diagnostic primers for Cryptosporidium. Lane 1=molecular weight marker; lane 2=*C. parvum* DNA; lane 3=*G. duodenalis* DNA; lane 4=human DNA; lane 5=faecal DNA; lane 6=*Tritrichomonas foetus* DNA; lane 7=*C. serpentis* DNA; lane 8=negative control (no DNA). Molecular weight marker was 100 bp ladder (Gibco BRL); kb=kilobases.

Figure 1B:
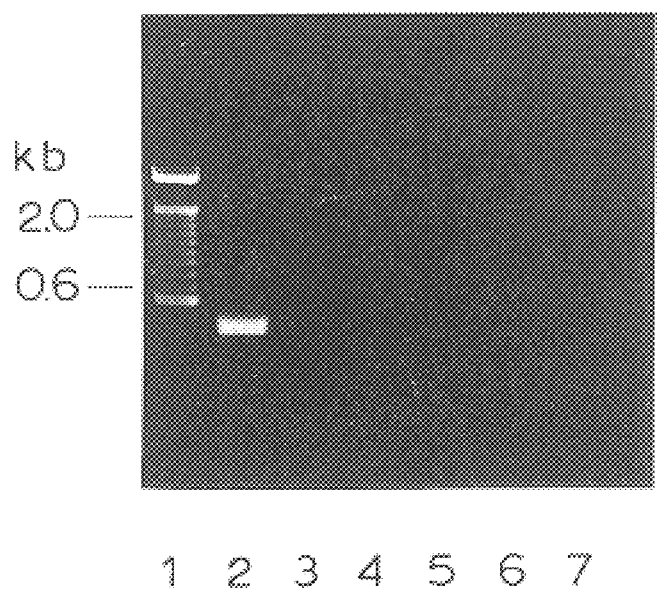

FIG. 1b shows the specificity testing of the CP1 primers. Lane 1=molecular weight marker; lane 2=*C. parvum* DNA; lane 3=*G. duodenalis* DNA; lane 4=human DNA; lane 5=faecal DNA; lane 6=*Tritrichomonas foetus* DNA; lane 7=negative control (no DNA). Molecular weight marker as in FIG. 1a.

Figure 2A:
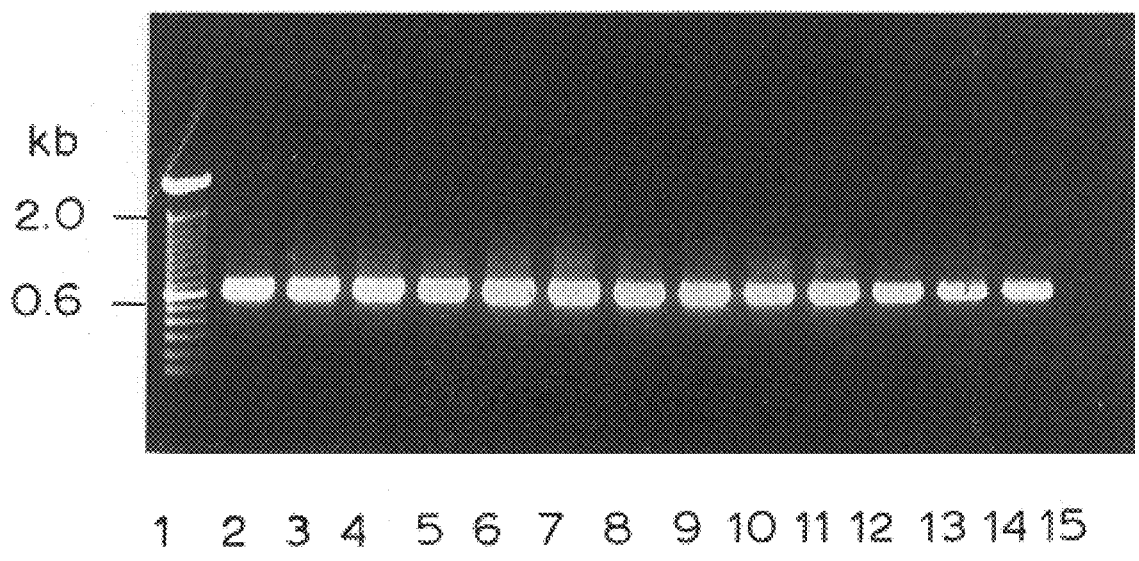

FIG. 2a represents an ethidium bromide stained 1% agarose gel showing products obtained from amplification performed on 13 of the 35 *Cryptosporidium parvum* isolates examined using the 021 primers. Lane 1=molecular weight marker; lane 2=L1; lane 3=H9; lane 4=C1; lane 5=H7; lane 6=H5; lane 7=H6; lane 8=H3; lane 9=H10; lane 10=H8; lane 11=H4; lane 12=H1; lane 13=C6; lane 14=H2; lane 15=negative control. Molecular weight marker as in FIG. 1a. Isolates H11–12; H15–H34; C1 and C7–9 were also tested and produced the desired 668 bp band upon amplification (data not shown).

Figure 2B:
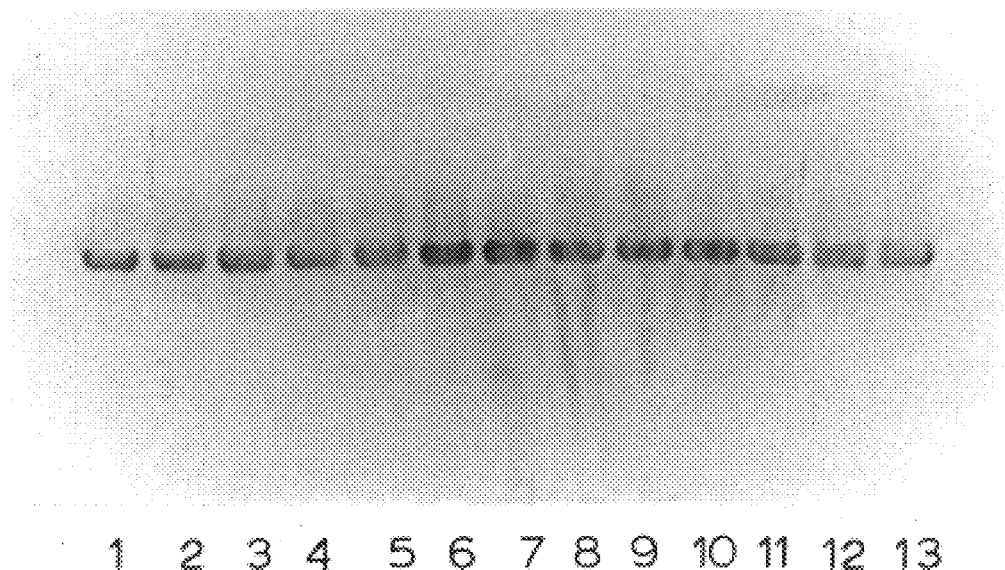

FIG. 2b illustrates parasite origin of the bands depicted in FIG. 2a. The gel depicted in FIG. 2a was blotted onto Hybond $N^+$ (Amersham) and probed with the internal oligonuleotide probes to confirm parasite origin of bands.

Figure 3:
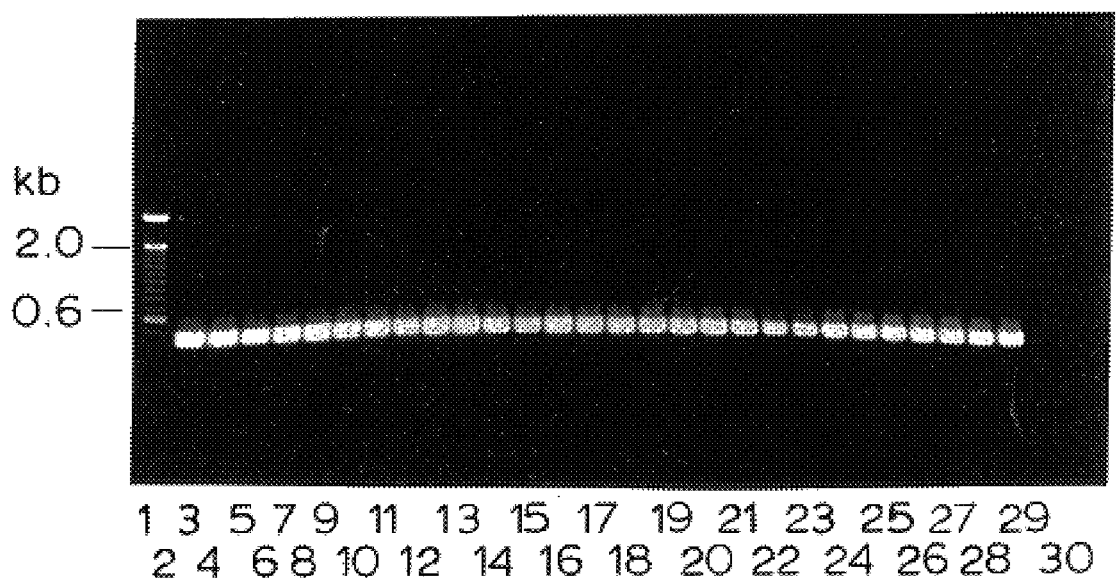

FIG. 3 represents an ethidium bromide stained 1% agarose gel showing products obtained from amplification performed on 28 of the 39 Cryptosporidium isolates examined using the CP1 primers. Lane 1=molecular weight marker; lane 2=H1; lane 3=H2; lane 4=H3; lane 5=H5; lane 6=H6; lane 7=H7; lane 8=H8; lane 9=H9; lane 10=H10; lane 11=H11; lane 12=H12; lane 13=15; lane 14=H16; lane 15=H17; lane 16=H18; lane 17=H19; lane 18=H20; lane 19=H21; lane 20=H22; lane 21=H23; lane 22=H24; lane 23=H25; lane 24=H26; lane 25=C1; lane 26=C2; lane 27=C6; lane 28=C7; lane 29=L1; lane 30=negative control. Isolates F1; F9; F10; F11; F20; F21; F22; F35; F36; F38 also amplified the correct 446 bp band.

Figure 4A:
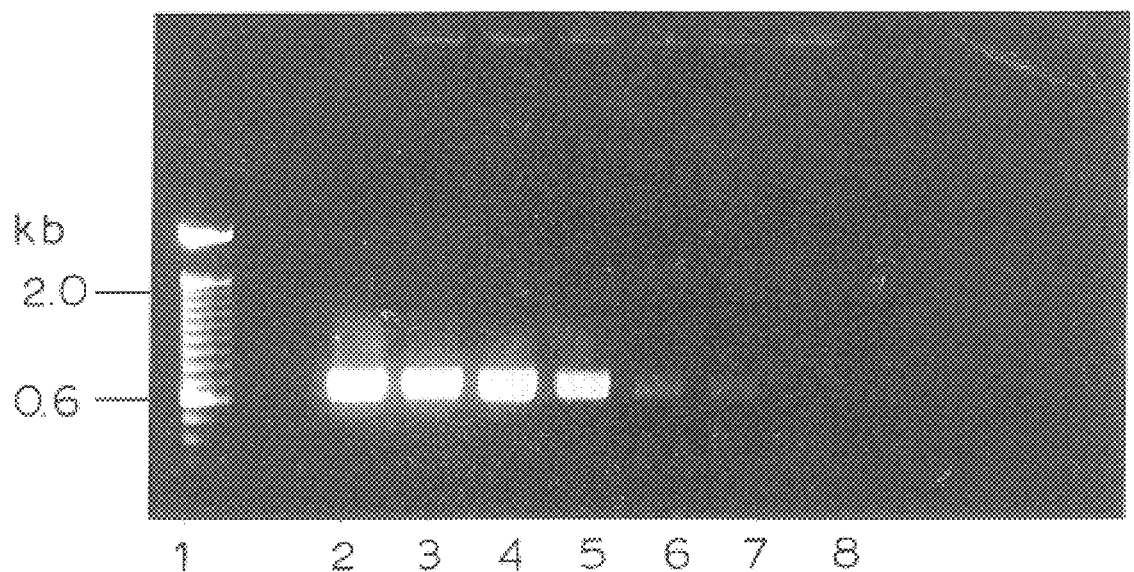

FIG. 4a represents an ethidium bromide stained 1% agarose gel showing the sensitivity of the 021 primers. Lane 1=molecular weight marker; lane 2=$1 \times 10^5$ *C. parvum* oocysts; lane 3=$1 \times 10^4$ *C. parvum* oocysts; lane 4=$1 \times 10^3$ *C. parvum* oocysts; lane 5=100 *C. parvum* oocysts; lane 6=10 *C. parvum* oocysts; lane 7=1 *C. parvum* oocys; and lane 8=negative control. Molecular weight marker as in FIG. 1a.

Figure 4B:
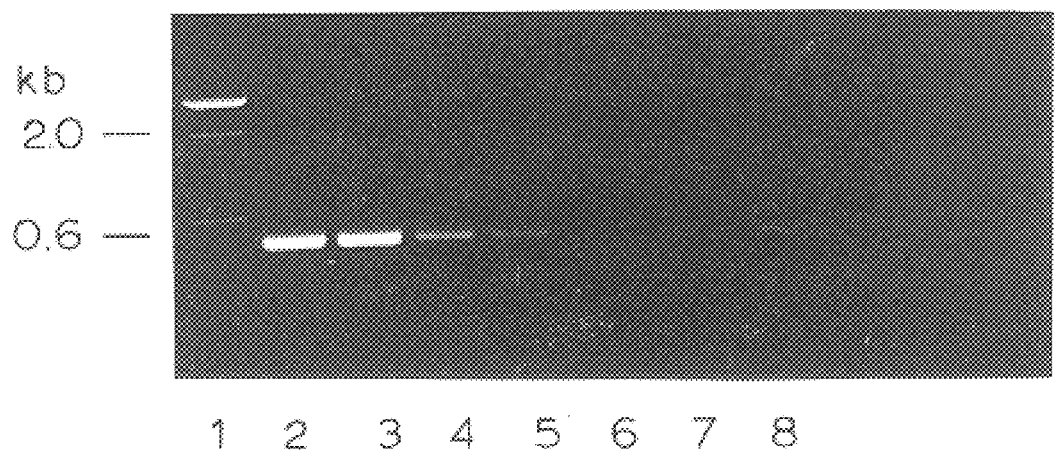

FIG. 4b represents an ethidium bromide stained 1% agarose gel showing the sensitivity of the CP primers. Lane 1=molecular weight marker; lane 2=1×10³ C. parvum oocysts; lane 3=100 C. parvum oocysts; lane 4=10 C. parvum oocysts; lane 5=1 C. parvum oocyst; lane 6=negative control (no DNA). Molecular weight marker as in FIG. 1a.

Figure 5A:
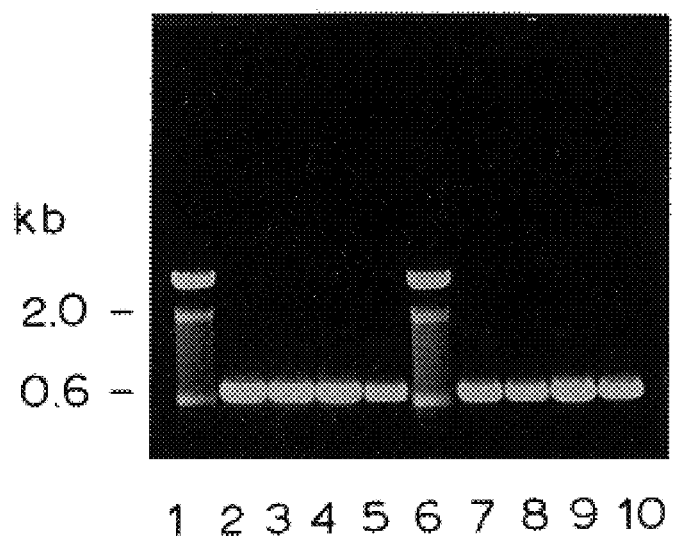

FIG. 5a represents an ethidium bromide stained 1% agarose gel showing direct amplification of Cryptosporidium DNA from faeces using the O21 primers. Lane 1=molecular weight marker, lane 2=H27; lane 3=H28; lane 4=H29; lane 5=H30; lane 6=molecular weight marker, lane 7=H31; lane 8=H32; lane 9=H33; lane 10=H34. Molecular weight marker as in FIG. 1a.

Figure 5B:
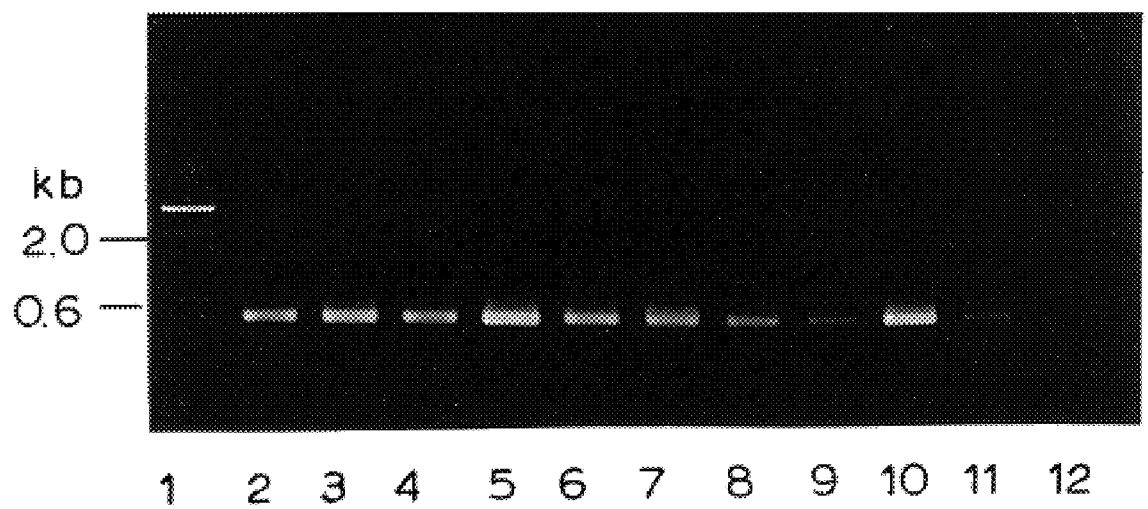

FIG. 5b shows amplification products from 9 faecal samples using the CP1 primers. Lane 1=molecular weight marker; lane 2=F1; lane 3=F9; lane 4=F10; lane 5=F11; lane 6=F20; lane 7=F21; lane 8=F22; lane 9=F35; lane 10=F36; lane 11=F38; lane 12=negative control.

FIGS. 6A–6N illustrate an alignment of Human and Calf sequences of the diagnostic O2 fragment. Figures are to be read in sequential order, i.e., FIGS. 6A to 6N.

EXAMPLES

Cryptosporidium Isolates

Isolates of Cryptosporidium are listed in Table 1, below. Cryptosporidium isolates for RAPD analysis were purified from faecal DNA by PBS-ether centrifugation followed by Ficoll-density centrifugation as described by Morgan, Constantine, O'Donoghue, Meloni, O'Brien & Thompson, (1995). "Molecular Characterisation of Cryptosporidium isolates from humans and other animals using RAPD (Random Amplified Polymorphic DNA) analysis. *American Journal of Tropical Medicine and Hygiene*" 52 559–564. All faecal samples were stored at 4° C. without preservatives for several weeks prior to analysis.

TABLE 1

Isolates of Cryptospridium used in this study

| Code | Host | Species | Geographic origin | Source |
|---|---|---|---|---|
| H1 | Human | C. parvum | Perth, Western Australia | PMH |
| H2 | Human | C. parvum | Narrogin, Western Australia | SHL |
| H3 | Human | C. parvum | Nannup, Western Australia | PMH |
| H4 | Human | C. parvum | Perth, Western Australia | PMH |
| H5 | Human | C. parvum | Perth, Western Australia | PMH |
| H6 | Human | C. parvum | Perth, Western Australia | PMH |
| H7 | Human | C. parvum | Perth, Western Australia | PMH |
| H8 | Human | C. parvum | Perth, Western Australia | SHL |
| H9 | Human | C. parvum | Perth, Western Australia | SHL |
| H10 | Human | C. parvum | Perth, Western Australia | PMH |
| H11 | Human | C. parvum | Perth, Western Australia | SHL |
| H12 | Human | C. parvum | Perth, Western Australia | SHL |
| H13 | Human | C. parvum | Horsham, Victoria | CVL |
| H14 | Human | C. parvum | Port Lincon, South Australia | CVL |
| H15 | Human | C. parvum | Perth, Western Australia | PMH |
| H16 | Human | C. parvum | Perth, Western Australia | PMH |
| H17 | Human | C. parvum | Perth, Western Australia | SHL |
| H18 | Human | C. parvum | Perth, Western Australia | PMH |
| H19 | Human | C. parvum | Perth, Western Australia | PMH |
| H20 | Human | C. parvum | Perth, Western Australia | PMH |
| H21 | Human | C. parvum | Perth, Western Australia | PMH |
| H22 | Human | C. parvum | Perth, Western Australia | SHL |
| H23 | Human | C. parvum | Perth, Western Australia | SHL |
| H24 | Human | C. parvum | Perth, Western Australia | SHL |
| H25 | Human | C. parvum | Perth, Western Australia | SHL |
| H26 | Human | C. parvum | Perth, Western Australia | SHL |
| H27 | Human | C. parvum | Perth, Western Australia | PMH |
| H28 | Human | C. parvum | Perth, Western Australia | PMH |

TABLE 1-continued

Isolates of Cryptospridium used in this study

| Code | Host | Species | Geographic origin | Source |
|---|---|---|---|---|
| H29 | Human | C. parvum | Bunbury, Western Australia | SHL |
| H30 | Human | C. parvum | Perth, Western Australia | SHL |
| H31 | Human | C. parvum | Perth, Western Australia | PMH |
| H32 | Human | C. parvum | Perth, Western Australia | SHL |
| H33 | Human | C. parvum | Perth, Western Australia | PMH |
| H34 | Human | C. parvum | Perth, Western Australia | PMH |
| F1 | Human | C. parvum | Perth, Western Australia | SHL |
| F9 | Human | C. parvum | Perth, Western Australia | SHL |
| F10 | Human | C. parvum | Newman, Western Australia | SHL |
| F11 | Human | C. parvum | Newman, Western Australia | SHL |
| F20 | Human | C. parvum | Perth, Western Australia | SHL |
| F21 | Human | C. parvum | Perth, Western Australia | SHL |
| F22 | Human | C. parvum | Perth, Western Australia | SHL |
| F35 | Human | C. parvum | Perth, Western Australia | PMH |
| F36 | Human | C. parvum | Perth, Western Australia | PMH |
| F38 | Human | C. parvum | Perth, Western Australia | SHL |
| C1 | Calf | C. parvum | Millicent, South Australia | CVL |
| C2 | Calf | C. parvum | Lucindale, South Australia | CVL |
| C3 | Calf | C. parvum | Meadows, South Australia | CVL |
| C4 | Calf | C. parvum | Lucindale, South Australia | CVL |
| C5 | Calf | C. parvum | Penola, South Australia | CVL |
| C6 | Calf | C. parvum | Willunga, South Australia | CVL |
| C7 | Calf | C. parvum | Penola, South Australia | CVL |
| C9 | Calf | C. parvum | Maryland, U.S.A. | USDA |
| L1 | Lamb/Deer | C. parvum | Edinburgh, Scotland | CVL |
| S1 | Snake | C. serpentis | Tanunda, South Australia | CVL |
| S2 | Snake | C. serpentis | Tanunda, South Australia | CVL |

(N.B. PMH = Princess Margaret Hospital, Perth, Western Australia; SHL = State Health Laboratories, Western Australia; CVL = Central Veterinary Laboratories, Southern Australia Dept. of Agriculture, Southern Australia ; MAH = Moredun Animal Health Ltd, Edinburgh, Scotland, and USDA = United States Department of Agriculture, Maryland, U.S.A.; N/A = not available).

DNA Isolation

For RAPD analysis, DNA was extracted from Cryptosporidium using the CTAB method described by Yap and Thompson (1987). "CTAB precipitation of cestode DNA". *Parasitology Today* 3: 220–222. Cryptosporidium oocysts were resuspended in 200 µl of lysis buffer containing, 0.25M Sucrose; 50 mM Tris-HCl; 50 mM EDTA; 8% Triton-X-100; pH 7.5. Oocysts were subjected to three freeze-thaw cycles and then 50 µl of a 10 mg/ml proteinase K solution was added. Samples were incubated for 1 hour at 55° C. and nucleic acid precipitated by the addition of 1 ml of 2% CTAB (cetyltrimethylammonium bromide). Following centrifugation, the pellet was dissolved in 250 µl of N.E. buffer (2.5 M NaCl, 10 mM EDTA, pH 7.7) and diluted with 250 µl of T.E. buffer (10 mM Tris-HCl, 1 mM EDTA, pH 7.5). Samples were subsequently chloroform extracted once, precipitated with 100% ethanol, washed with 70% ethanol and resuspended in T.E. buffer. DNA was similarly isolated from human blood, human faeces, *Giardia duodenalis*, *Tritrichomonas foetus* and *C. seprentis* for cross-hybridisation studies.

PCR Conditions and Primers

The selection of DNA primer(s) or probe(s) by the construction and screening of genomic DNA libraries is a laborious and expensive exercise. However by using the Random Amplified Polymorphic DNA (RAPD) technique described hereafter, for the development of diagnostic probes or primers, the process of selecting such nucleotide sequences is greatly simplified. In this technique, small amounts of DNA are subjected to PCR using a single oligonucleotide of random sequence as a primer. The amplification products are resolved on agarose or polyacrylamide gels giving rise to a pattern that is strain specific. Many of the products generated by RAPD-PCR are derived from repetitive DNA sequences. As these sequences are frequently species-specific, RAPD-PCR is potentially a quick method for developing species-specific diagnostic PCR primers and probes RAPD reactions were performed as described by Morgan, Constantine, O'Donoghue, Meloni, O'Brien & Thompson, (1995). "Molecular Characterisation of Cryptosporidium isolates from humans and other animals using RAPD (Random Amplified Polymorphic DNA) analysis. *"American Journal of Tropical Medicine and Hygiene"* 52 559–564. A range of primers were tested and are listed below.

| | |
|---|---|
| R-2817 | 5' GCTTGGTCTGCTCAATGTGG 3' |
| INS | 5' ACAGGGGTGTGGGG 3' |
| PER | 5' GACNGGNACNGG 3' |
| Y22 | 5' CTCTGGGTGTCGTGC 3' |
| SP6 | 5' GATTTAGGTGACACTATAG 3' |
| [GAA]$^5$ | 5' GAAGAAGAAGAAGAA 3' |
| [GACA]$^4$ | 5' GACAGACAGACAGACA 3' |
| R4 | 5' AGTCGAACCCTGATTCTCCGCCAGG 3' |

Vacuum Blots, Dot Blots and DNA Hybridisation

RAPD gels were vacuum blotted (BioRad) onto Hybond N$^+$ ([Amersham]) membranes using 20×SSC (0.3 M Na$_3$citrate; 3 M NaCl; pH adjusted to 7.0) as the transfer medium. Following transfer, DNA was UV cross-linked to the membranes using a GS Gene-Linker™ UV cross-linker (BioRad). Probe labelling was conducted using two different non-radioactive labelling systems. The ECL (Enhanced Chemiluminescence) direct labelling kit supplied by Amersham, was used to label all double stranded DNA and the DIG (digoxigenin) oligonucleotide 3'-end labelling and detection kit supplied by Boehringer Mannheim was used to label oligonucleotides. For most hybridisations, 100 ng of DNA (at a concentration of 10 ng/μl) was labelled and used in a 10 ml hybridisation volume. All hybridisations were carried out in a Hybaid™ rotisserie oven (BioRad). For dot-blots, DNA was transferred to Hybond N$^+$ membrane (Amersham), using a vacuum manifold (BioRad). DNA was bound to the membrane using the UV cross-linking procedure described above.

Southern blots of RAPD profiles were hybridised to DNA isolated from human blood, *Giardia duodenalis*, human faeces and *Cryptosporidium parvum*. RAPD bands which hybridised only to Cryptosporidium DNA and not to the other DNA's tested were chosen for further analysis. Primers R-2817, INS, PER, Y22, SP6, [GAA]$^5$ and [GACA]$^4$ all produced profiles which cross-reacted to varying degrees with human, faecal or Giardia DNA. The primer R4, however, produced a simple profile which cross-reacted with Cryptosporidium DNA only (data not shown). A band of approximately 750 bp was purified from a low-melting point gel using the syringe method described by Li. & Ownby (1993). "A rapid method for extraction of DNA from agarose gels using a syringe." *Biotechniques* 15: 976–978, reamplified and shown to be specific for Cryptosporidium by dot-blots. The band, designated 021 was then cloned and sequenced.

Cloning of PCR Products

Bands specific for Cryptosporidium were ligated directly into the pGEM T-Vector (Promega). Ligation products were transformed into *Escherichia coli* HB101 and white colonies were screened using PCR. Half of each white colony was removed with a sterile toothpick and added to a 50 μl solution of TE buffer containing 1% Triton-X-100. The toothpick was swirled around to dislodge the cells and then discarded. These tubes were subsequently incubated at 95° C. for 10 min to lyse the cells, spun for 5 min to remove cellular debris and the supernatant transferred to a clean tube.

A 5 μl aliquot of this supernatant was used in a PCR reaction, with the M13 foreword and reverse primers. Briefly, 5 μl of crude lysate was amplified in 67 mM Tris-HCL (pH 7.6), 16.6 mM (NH$_4$)$_2$SO$_4$; 2 mM MgCl$_2$; 200 μM of each dNTP; 12.5 pmoles of each primer; 0.5 units of Tth Plus (Biotech International) and sterile distilled water. Reactions were performed on an OmniGene thermal cycler (Hybaid), using the following cycling conditions. One cycle of 94° C. for 2 min; 55° C. for 2 min and 72° C. for 2 min, followed by 30 cycles of 94° C. for 30 seconds; 55° C. for 1 min and 72° C. for 2 min with a final cycle of 94° C. for 30 seconds; 55° C. for 1 min and 72° C. for 10 min. An aliquot (5–10 μl) of the amplified product was then run on a 1% agarose gel and checked for size.

At least 10 white colonies for each ligation were checked for the presence of inserts using the PCR protocol described above. Inserts were cut out using Sac II and Pst 1 restriction enzymes (Pharmacia), electrophoresed on a 1% low-melting point agarose gel and the insert purified from the gel using the syringe method. At this point, inserts were again checked for specificity by dot blots and Cryptosporidium-specific inserts were chosen for sequencing.

Sequencing and Synthesis of Primers

Sequencing was carried out using the Taq DyeDeoxy™ Terminator Cycle Sequencing Kit supplied by Applied Biosystems. Sequences were aligned using the Seqed and DNA strider programs and compared with Genebank and EMBL databases for sequence homology. A number of primer sequences were designed from the 021 sequence using the computor program Amplify™ and oligonucleotides were synthesised by DNA Express.

Primers

The 021 forward and 021 reverse primers which produced a 668 bp fragment upon amplification of *Cryptosporidium parvum* DNA are listed below. An oligonucleotide internal to the sequence amplified by the 021 primers was also synthesised for use as a probe to confirm parasite origin of the amplified product. A second set of primers, designated CP1 forward and reverse and an internal oligonucleotide designated CPI were also designed from the 021 sequence. These primers produced an approximately 426 bp fragment upon amplification of Cryptosporidium DNA.

| | |
|---|---|
| 021 F | 5' GGTACTGGATAGATAGTGGA 3' |
| 021 R | 5' TCGCACGCCCGGATTCTGTA 3' |
| Oligo | 5' AGTCCCGTATCAGTTCGAGA 3' |
| CP1 F | 5' GAGATTCTGAAATTAATTGG 3' |
| CP1 R | 5' CCTCCTTCGTTAGTTGAATCC 3' |
| CPI | 5' GTTGGCTTATAGATTCTGAGC 3' |

The sequence of the diagnostic fragment is shown below with the positions at which the primers bind underlined. The CP1 forward and reverse primers are shown binding inside the sequence specified by the 021 primers and produce a 426 bp product upon amplification.

GATGGTACTGGATAGATAGTGGAAGTCCCGTATCAGTTCGAGATTCTGAAATTAATTGG

ACATCAAGTTATAAAGCAAGCTGGTTATTAAGATTCAAATTTCCCTTTGAAAAGTGTGG

CTTTTTTGATATTGGAGGGTTAGGAAGAAGGCCGTGTTGGCTTATAGATTCTGAGCTTT

CTTGTGCAGTTTGTGGTACAGTAGCTTATGATTCTGGTGGGCTGAATCCCAATAAATAT

TCAGAGCTAATTAAGCAGACTGATGAAATTATTAGTAAAGAGCCAAAGCTTGATCTTCC

AGGTTACAATAATTTGAACTGTACAGATGCTTGGGAGAATAATTTATCAGTTGGTCTTT

GTCAAAATGTCTCAAATATCCTGGACTCAGCTTGGAGCTCGTATCAGAGTTCGTTAAAC

TTTCCTAGTATCAACTTTAACTGGAAAGAGGATTCAACTAACGAAGGAGGGGACCAAGT

TTACCATAATTCTTATTTGGATCTTCCAAGGTATAAGCAGAAGAAAACATTTTATTGGG

ATCAGGATCCAGGTACTATTCCAGCTTTGTCTGATGAAATGAAGCTCATTGGTTTAAGC

GCTCAACCAACATACCATCCTTTGGATAGAAGCTCATCTGGAAGTTTTGAGTCTGATAG

TACAGAATCCGGGCGTGCGAATGAAGAAAGAAACGATAC

Diagnostic PCR Conditions

PCR conditions for the 021 diagnostic PCR primers consisted of 67 mM Tris-HCL (pH 7.6), 16.6 mM $(NH_4)_2SO_4$; 1.5 mM $MgCl_2$; 200 μM of each dNTP; 6.5 pmoles of each primer; 0.25 units of Tth Plus (Biotech International) and sterile distilled water. Reactions were performed on an OmniGene thermal cycler (Hybaid), using the following cycling conditions. One cycle of 94° C. for 2 min; 58° C. for 2 min and 72° C. for 2 min, followed by 40 cycles of 94° C. for 30 seconds; 58° C. for 1 min and 72° C. for 2 min with a final cycle of 94° C. for 30 seconds; 58° C. for 1 min and 72° C. for 10 min. PCR conditions for the CP1 primers were essentially the same except that 2 mM $MgCl_2$ and an annealing temperature of 59° C. was used.

Diagnostic Test

For sensitivity testing, crude oocyst preparations were resuspended in 10 μl of T.E. Decreasing concentrations of oocyst suspensions were prepared by serial dilutions. For direct PCR analysis of faecal samples, 0.5 g of faeces was mixed with 4 ml PBS and this slurry was then diluted 1 in 20 in T.E. Samples were then freeze-thawed 3 times, boiled for 5 min, spun for 1 min to remove debris and then 5–10 μl of the supernatant was added directly to the PCR reaction.

The above oligonucleotide sequences are unique in that a comparison of the sequence information obtained from the 021 clone with Genebank and EMBL databases produced no homology of any significance. The specificity of the primers designed from the 021 clone was tested by performing PCR reactions on DNA extracted from *Giardia duodenalis*, human blood, human faeces, *Tritrichomonas foetus*, and *C. serpentis*. With both sets of primers, DNA of the correct size was amplified from *Cryptosporidium parvum* DNA only. No amplification was seen with any of the other DNA's tested (see FIGS. 1a and b).

The primers were also tested on Cryptosporidium of both human and bovine origin and the PCR products confirmed by hybridisation to the internal oligonucleotide. These diagnostic primers were then used to amplify over 40 different isolates of *Cryptosporidium parvum* of both human and bovine origin (listed in Table 1), to determine if the primers would recognise some or all isolates. All isolates tested produced the correct sized upon amplification (see FIGS. 2a; 2b and 3).

The gel depicted in FIG. 2a was then blotted onto Hybond $N^+$ (Amersham) and probed with the internal oligonuleotide probes to confirm parasite origin of bands (FIG. 2b).

The amplification products of the CPF primers were also probed with an internal oligonucleotide to confirm parasite origin of the bands. In all cases the 446 bp amplification product hybridised strongly with the internal olifo indicating that the reaction was specific for Cryptosporidium (data not shown).

The detection limits of the primers were found to be as high as one oocyst (see FIG. 4a) with both the 021 and the CP1 primers (see FIG. 4b) when amplifying from crude preparations of oocysts.

The primers were also used to reproducibly amplify Cryptosporidium directly from boiled faeces (see FIG. 5a). Most of the eight faecal samples tested contained relatively low numbers of oocysts (ranging from $1 \times 10^3$ to $5 \times 10^5$ oocysts per gram of faeces, with one sample, H29, containing $1.5 \times 10^6$ oocysts per g of faeces). One sample, H27, unlike the other samples, was a solid stool and it was necessary to perform a crude PBS-ether extraction of that sample in order to obtain a reproducible amplification product (see FIG. 5a).

FIG. 5b shows amplification products from 9 faecal samples using the CP1 primers. Lane 1=molecular weight marker; lane 2=F1; lane 3=F9; lane 4=F10; lane 5=F11; lane 6=F20; lane 7=F21; lane 8=F22; lane 9=F35; lane 10=F36; lane 11=F38; lane 12=negative control.

The sequences of two human and two calf isolates of *Cryptosporidium parvum* were compared along the length of the diagnostic fragment to determine the extent of sequence conservation between isolates (see FIGS. 6A–6N). Direct PCR sequencing was carried out using the Taq DyeDeoxy™ Terminator Cycle Sequencing Kit supplied by Applied Biosystems. Sequences were aligned using the CLUSTAL V multiple sequence alignment program. The alignment shows the sequence to be conserved between isolates but with a number of sequence differences between the human and calf isolates. These findings are in keeping with RAPD analysis on these isolates described by Morgan, Constantine, O'Donoghue, Meloni, O'Brien & Thompson, (1995). "Molecular Characterisation of Cryptosporidium isolates from humans and other animals using RAPD (Random Amplified Polymorphic DNA) analysis. "*American Journal of Tropical Medicine and Hygiene*" 52 559–564, which reported genetic differences between human and calf isolates. The observed differences between the human and calf isolates is not sufficient to interfere with primer binding and both human and calf isolates are amplified using both the 021 and the CP1 primers (primer sequences are underlined). Given the differences between the human and calf isolates however, it would be possible to construct primers which could differentiate between human and animal isolates (ie a set of primers which would amplify human isolates only and a second set which would amplify calf/animal isolates only). Primers which are specific for animal or human isolates would be very useful in transmission studies and also for environmental analysis in determining the likely source of contamination of water supplies (ie human or animal).

The above mentioned sequence was analysed to determine whether or not the sequence was from a coding or non-coding section of DNA. A number of computer programs were used including CODON PREFERENCE which is a frame-specific gene finder that tries to recognise protein coding sequences by virtue of the similarity of their codon usage to a codon frequency table or by the bias of their composition (usually GC) in the third position of each codon. Analysis of the sequence using these programs however, suggests that the 021 fragment is unlikely to contain coding regions.

RAPD analysis was used to develop diagnostic primers for *Cryptosporidium parvum* which have been shown to be both specific and also sensitive. Both the 021 and the CP1 primers appear to be very specific for Cryptosporidium, can detect as little as one oocyst and can amplify Cryptosporidium directly from boiled faeces. Over 47 different isolates of *Cryptosporidium parvum* of both human and bovine origin from diverse geographic locations were screened using these primers and all amplified the correct sized band, indicating that the sequence defined by the primers is conserved amongst isolates.

The specificity testing of the RAPD primers did not include *Cryptosporidium baileyi, Cryptosporidium meleagridis* or *Cryptosporidium muris* DNA, as a source of this material was not readily available. Although *Cryptosporidium muris* has been reported in cattle in the United States, and oocysts resembling *Cryptosporidium baileyi* were recovered from an immunocompromised human patient, these species of Cryptosporidium are not commonly reported in livestock and particularly not from humans. Further optimisation of the assay is required to enable the amplification of all Cryptosporidium isolates directly from faeces without any prior purification.

The RAPD primers described herein could be used both in the diagnosis of Cryptosporidium from faecal samples and also in environmental monitoring. The level of skill required by microscopic identification of Cryptosporidium oocysts, the low sensitivity of current diagnostic methods and varying expertise among laboratories and technicians can result in many cases of mild cryptosporidial infection remaining undiagnosed. A simple PCR detection system employing primers of the present invention should greatly improve the detection and diagnosis of Cryptosporidium.

Outbreaks of cryptosporidiosis in child day care centres are frequently reported (Alpert et al. 1986; Crawford et al. 1988; Diers & McCallister 1989; Ferson & Young 1992; Hanna & Brooks 1995), and family members are often affected during such outbreaks. A proportion of each group is asymptomatic and can act as carriers of infection to relatives and the community. Therefore, the public health problem of transmission to the community from these centres is a significant one and needs further evaluation and control. Investigations undertaken during outbreaks of diarrhoea however, have frequently used limited diagnostic testing that have tended to incriminate agents that are easily identifiable in standard microbiological laboratories (Thompson 1994). Sensitive molecular-based tools such as the PCR primers described here will allow more accurate molecular-epidemiological studies to be carried out to determine not only the true prevalence of Cryptosporidium in the community, but also the risk factors associated with infection.

A recent survey in the United States conducted by Clancy et al. (1994) "Commercial labs: how accurate are they?" *Journal of the American Water Works Association.* 86: 89–97, revealed that commercial laboratories showed a lack of proficiency in testing water samples for Giardia and Cryptosporidium. With the implementation in 1995 of the Information Collection Rule (ICR) in the United States which makes testing for Giardia and Cryptosporidium in water systems serving more than 10,000 people mandatory, the development of accurate and sensitive testing for Cryptosporidium is of great importance.

As a result of this study, highly sensitive and specific diagnostic PCR primers have been developed for Cryptosporidium.

REFERENCES

ALPERT, G. L. M., BELL, C. E., KIRKPATRICK L. D., BUDNICK, J. M., CAMPOS, H. M., FRIEDMAN, H. M. AND PLOTKIN, S. A. (1986) Outbreak of cryptosporidiosis in a day-care centre. Pediatrics. 77, 152–156.

CRAWFORD, F. G., VERMUND S. H., MA, J. Y. AND DECKELBAUM, R. J. (1988). Asymptomatic cryptosporidiosis in a New York City day care centre. Paediatric Infectious Disease Journal. 7, 806.

DIERS, J. & McCALLISTER G. L. (1989). Occurrence of Cryptosporidium in home daycare centres in West-Central Colorado. Journal of Parasitology. 75, 637–638.

FERSON, M. J. & YOUNG, L. C. (1992). Cryptosporidium and coxsackievirus B5 causing epidemic diarrhoea in a child-care centre. Medical Journal of Australia. 156, 813.

HANNA J. & BROOKS, D. (1995). Cryptosporidiosis in a child day-care centre. Communicable Disease Intelligence. 19, 6–7.

THOMPSON, S. C. (1994). Infectious diarrhoea in children—controlling transmission in the child care setting. Journal of Paediatric Child Health. 30, 210–219.

We claim:

1. A purified and isolated Cryptosporidium DNA sequence comprising the nucleotide sequence:

GATGGTACTGGATAGATAGTGGAAGTCCCGTATCAGTTCGAGATTCTGAAA
TTAATTGGACATCAAGTTATAAAGCAAGCTGGTTATTAAGATTCAAATTTC
CCTTTGAAAAGTGTGGCTTTTTTGATATTGGAGGGTTAGGAAGAAGGCCGT
GTTGGCTTATAGATTCTGAGCTTTCTTGTGCAGTTTGTGGTACAGTAGCTT
ATGATTCTGGTGGGCTGAATCCCAATAAATATTCAGAGCTAATTAAGCAGA
CTGATGAAATTATTAGTAAAGAGCCAAAGCTTGATCTTCCAGGATACAATA
ATTTGAACTGTACAGATGCTTGGGAGAATAATTTATCAGTTGGTCTTTGTC
AAAATGTCTCAAATATCCTGGACTCAGCTTGGAGCTGGTATCAGAGTTCGT
TAAACTTTCCTAGTATCAACTTTAACTGGAAAGAGGATTCAACTAACGAAG
GAGGGGACCAAGTTTACCATAATTCTTATTTGGATCTTCCAAGGTATAAGC
AGAAGAAAACATTTTATTGGGATCAGGATCCAGGTACTATTCCAGCTTTGT
CTGATGAAATGAAGCTCATTGGTTTAAGCGCTCAACCAACATACCATCCTT
TGGATAGAAGCTCATCTGGAAGTTTTGAGTCTGATAGTACAGAATCCGGGC
GTGCGAATGAAGAAAGAAACGATAC (SEQ ID NO. 1).

2. A method for detecting and/or identifying the presence of Cryptosporidium genomic material in a sample, said method comprising the steps of:
(i) selecting at least a primer(s) or probe from nucleotide sequence according to claim 1; and
(ii) using the primer(s) or probe to detect and/or identify the presence of Cryptosporidium genomic material in the sample.

3. A method according to claim 2 wherein Cryptosporidium genomic material in the sample is detected by a hybridisation assay.

4. A method according to claim 2 wherein the probe or primer(s) is at least 5 nucleotides in length.

5. A method according to claim 2 wherein the probe or primer(s) is about 10 to 50 nucleotides in length.

6. A method according to claim 2 wherein the probe or primer(s) is about 20 to 24 nucleotides in length.

7. A method according to claim 3 wherein the probe or primer(s) is selected from from the group of sequences consisting of:

| | |
|---|---|
| GGTACTGGATAGATAGTGGA; | (SEQ ID NO. 2); |
| TCGCACGCCCGGATTCTGTA; | (SEQ ID NO. 3); |
| AGTCCCGTATCAGTTCGAGA; | (SEQ ID NO. 4); |
| ACTGGATAGATAGTGGAAGT; | (SEQ ID NO. 5); |
| TTTCTTTCTTCATTCGCACG; | (SEQ ID NO. 6); |
| GTGGAAGTCCCGTATCAGTC; | (SEQ ID NO. 7); |
| ACGCCCGGATTCTGTACTAT; | (SEQ ID NO. 8); |
| GATAGATAGTGGAAGTCCCG; | (SEQ ID NO. 9); |
| ACGCCCGGATTCTGTACTAT; | (SEQ ID NO. 8); |
| CTGAAATTAATTGGACATCA; | (SEQ ID NO. 10); |
| GTACTATCAGACTCAAAACT; | (SEQ ID NO. 11); |
| GTGGTACTGGATAGATAGTG; | (SEQ ID NO. 12); |
| GTATCGTTTCTTTCTTCATT; | (SEQ ID NO. 13); |
| TGGTACTGGATAGATAGTGG; | (SEQ ID NO. 14); |
| TATCGTTTCTTTCTTCATTC; | (SEQ ID No. 15); |
| TAGATAGTGGAAGTCCCGTA; | (SEQ ID NO. 16); |
| TCTTCATTCGCACGCCCGGA; | (SEQ ID NO. 17); |
| ATAGTGGAAGTCCCGTATCA; | (SEQ ID NO. 18); |
| TTTCTTCATTCGCACGCCCG; | (SEQ ID NO. 19); |
| CTGGATAGATAGTGGAAGTC; | (SEQ ID NO. 20); |
| CGTTTCTTTCTTCATTCGCA; | (SEQ ID NO. 21); |
| TAATTGGACATCAAGTATAA; | (SEQ ID NO. 22); |
| GTACTATCAGACTCAAAACT; | (SEQ ID NO. 11); |
| TCTGAAATTAATTGGACATC; | (SEQ ID NO. 23); |
| CTTCCAGATGAGCTTCTATC; | (SEQ ID NO. 24); |
| GGTGGTACTGGATAGATAGT; | (SEQ ID NO. 25); |
| GGTATCGTTTCTTTCTTCAT; | (SEQ ID NO. 26); |
| GAGATTCTGAAATTAATTGG; | (SEQ ID NO. 27); |
| GTTGGCTTATAGATTCTGAGC; | (SEQ ID NO. 28); |
| GGTTATTAAGATTCAAATTTCC; | (SEQ ID NO. 29); |
| TCCCGTATCAGTTCGAGATTCTG; | (SEQ ID NO. 30); |
| CGAACTCTGATACGAGCTCCAAGC; | (SEQ ID NO. 31); |
| ATTCGAGATTCTGAAATTAATTGG; | (SEQ ID NO. 32); |
| GAATAGTACCTGGATCCTGATCCC; | (SEQ ID NO. 33); |
| GATATTGGAGGGTTAGGAAGAAGG; | (SEQ ID NO. 34); |
| CTGTACAGTTCAAATTATTGTAACC; | (SEQ ID NO. 35); |
| GACTGATGAAATTATTAGTAAAGAGC; | (SEQ ID NO. 36); |
| CCTCCTTCGTTAGTTGAATCCTC; | (SEQ ID NO. 37); |
| TCGCACGCCCGGATTCTGTA; | (SEQ ID NO. 3); |
| CAGTTCAAATTATTGTAGCC; | (SEQ ID NO. 38); |
| GTTCGAGATTCTGAAATTAATTGG; | (SEQ ID NO. 39); |
| GTCCCGTATCAGTTCGAGATTCTG; | (SEQ ID NO. 40); |
| GGAGGGTTAGGAAGAAGGCCGTG; | (SEQ ID NO. 41); |
| GCTTGGGAGAATAATTTATCAG; | (SEQ ID NO. 42); |
| GGGATCAGGATCCAGGTACTATTC; | (SEQ ID NO. 43); |
| GTATCGTTTCTTTCTTCATTCGC; | (SEQ ID NO.44); |
| GGACCAAGTTTACCATAATTC; | (SEQ ID NO. 45); |
| GGAGAATAATTTATCAGTTGGTC; | (SEQ ID NO. 46); |
| CAAGGTATAAGCAGAAGAAAAC; | (SEQ ID NO. 47); |
| CGCACGCCCGGATTCTGTACTATC; | (SEQ ID NO. 48); |
| ATGTCTCAAATATCCTGGACTCAG; | (SEQ ID NO. 49); |
| GTACTGGATAGATAGTGGAAGTC; | (SEQ ID NO. 50); |

CACGGCCTTCTTCCTAACCCTCC; (SEQ ID NO. 51);

and

GGAAGTCCCGTATCAGTTCGAG (SEQ ID NO. 52).

8. A method for detecting and/or identifying microorganisms of the genus Cryptosporidium, comprising the steps of:

(i) selecting at least a set of primers from the nucleotide sequence defined in claim 1 which are specific for Cryptosporidium DNA;

(ii) mixing the primers with a sample suspected of containing Cryptosporidium DNA;

(iii) amplifying the product(s) of step (ii) by the polymerase chain reaction; and (iv) detecting the presence of the product of step (iii).

9. A method according to claim 7 wherein the primers are selected from the group of primer pairs consisting of:

| | | |
|---|---|---|
| (i) | 5' ACTGGATAGATAGTGGAAGT 3' | (SEQ ID NO. 5); |
| | 5' TTTCTTTCTTCATTCGCACG 3' | (SEQ ID NO. 6); |
| (ii) | 5' GTGGAAGTCCCGTATCAGTC 3' | (SEQ ID NO. 7); |
| | 5' ACGCCCGGATTCTGTACTAT 3' | (SEQ ID NO. 8); |
| (iii) | 5' GATAGATAGTGGAAGTCCCG 3' | (SEQ ID NO. 9); |
| | 5' ACGCCCGGATTCTGTACTAT 3' | (SEQ ID NO. 8); |
| (iv) | 5' CTGAAATTAATTGGACATCA 3' | (SEQ ID NO. 10); |
| | 5' GTACTATCAGACTCAAAACT 3' | (SEQ ID NO. 11); |
| (v) | 5' GTGGTACTGGATAGATAGTG 3' | (SEQ ID NO. 12); |
| | 5' GTATCGTTTCTTTCTTCATT 3' | (SEQ ID NO. 13); |
| (vi) | 5' TGGTACTGGATAGATAGTGG 3' | (SEQ ID NO. 14); |
| | 5' TATCGTTTCTTTCTTCATTC 3' | (SEQ ID NO. 15); |
| (vii) | 5' TAGATAGTGGAAGTCCCGTA 3' | (SEQ ID NO. 16); |
| | 5' TCTTCATTCGCACGCCCGGA 3' | (SEQ ID NO. 17); |
| (viii) | 5' ATAGTGGAAGTCCCGTATCA 3' | (SEQ ID NO. 18); |
| | 5' TTTCTTCATTCGCACGCCCG 3' | (SEQ ID NO. 19); |
| (ix) | 5' CTGGATAGATAGTGGAAGTC 3' | (SEQ ID NO. 20); |
| | 5' CGTTTCTTTCTTCATTCGCA 3' | (SEQ ID NO. 21); |
| (x) | 5' TAATTGGACATCAAGTATAA 3' | (SEQ ID NO. 22); |
| | 5' GTACTATCAGACTCAAAACT 3' | (SEQ ID NO. 11); |
| (xi) | 5' TCTGAAATTAATTGGACATC 3' | (SEQ ID NO. 23); |
| | 5' CTTCCAGATGAGCTTCTATC 3' | (SEQ ID NO. 24); |
| (xii) | 5' GGTGGTACTGGATAGATAGT 3' | (SEQ ID NO. 25); |
| | 5' GGTATCGTTTCTTTCTTCAT 3' | (SEQ ID NO. 26); |
| (xiii) | 5' GGTACTGGATAGATAGTGGA 3' | (SEQ ID NO. 2); |
| | 5' TCGCACGCCCGGATTCTGTA 3' | (SEQ ID NO. 3); |
| (xiv) | 5' GAGATTCTGAAATTAATTGG 3' | (SEQ ID NO. 27); |
| | 5' CCTCCTTCGTTAGTTGAATCC 3' | (SEQ ID NO. 53); |
| (xv) | 5' GTTGGCTTATAGATTCTGAGC 3' | (SEQ ID NO. 28); |
| | 5' CAGTTCAAATTATTGTAGCC 3' | (SEQ ID NO. 38); |
| (xvi) | 5' GAGATTCTGAAATTAATTGG 3' | (SEQ ID NO. 27); |
| | 5' CAGTTCAAATTATTGTAACC 3' | (SEQ ID NO. 54); |
| (xvii) | 5' GTTGGCTTATAGATTCTGAGC 3' | (SEQ ID NO. 28); |

-continued

```
           5' CCTCCTTCGTTAGTTGAATCC 3'       (SEQ ID NO. 53);
(xviii)    5' TAATTGGACATCAAGTTATAAAGC 3'    (SEQ ID NO. 55);
           5' GGAAGATCCAAATAAGAATTATGG 3'    (SEQ ID NO. 56);
(xix)      5' GGTTATTAAGATTCAAATTTCC 3'      (SEQ ID NO. 29);
           5' CGAACTCTGATACGAGCTCCAAGC 3'    (SEQ ID NO. 31);
(xx)       5' TCCCGTATCAGTTCGAGATTCTG 3'     (SEQ ID NO. 30);
           5' CGAACTCTGATACGAGCTCCAAGC 3'    (SEQ ID NO. 31);
(xxi)      5' GTTCGAGATTCTGAAATTAATTGG 3'    (SEQ ID NO. 39);
           5' CGAACTCTGATACGAGCTCCAAGC 3'    (SEQ ID NO. 31);
(xxii)     5' TAATTGGACATCAAGTTATAAAGC 3'    (SEQ ID NO. 55);
           5' CGAACTCTGATACGAGCTCCAAGC 3'    (SEQ ID NO. 31);
(xxiii)    5' GGTTATTAAGATTCAAATTTCC 3'      (SEQ ID NO. 29);
           5' CGAACTCTGATACGAGCTCCAAGC 3'    (SEQ ID NO. 34);
(xxiv)     5' TCCCGTATCAGTTCGAGATTCTG 3'     (SEQ ID NO. 30);
           5' GAATAGTACCTGGATCCTGATCCC 3'    (SEQ ID NO. 33);
(xxv)      5' TAATTGGACATCAAGTTATAAAGC 3'    (SEQ ID NO. 55);
           5' GAATAGTACCTGGATCCTGATCCC 3'    (SEQ ID NO. 33)
(xxvi)     5' GGTTATTAAGATTCAAATTTCC 3'      (SEQ ID NO. 29);
           5' GAATAGTACCTGGATCCTGATCCC 3'    (SEQ ID NO. 33);
(xxvii)    5' TCCCGTATCAGTTCGAGATTCTG 3'     (SEQ ID NO. 30);
           5' GGAAGATCCAAATAAGAATTATGG 3'    (SEQ ID NO. 56);
(xxviii)   5' GTTCGAGATTCTGAAATTAATTGG 3'    (SEQ ID NO. 39);
           5' GGAAGATCCAAATAAGAATTATGG 3'    (SEQ ID NO. 56);
(xxix)     5' GGTTATTAAGATTCAAATTTCC 3'      (SEQ ID NO. 29);
           5' GGAAGATCCAAATAAGAATTATGG 3'    (SEQ ID NO. 56);
(xxx)      5' ATTCGAGATTCTGAAATTAATTGG 3'    (SEQ ID NO. 32);
           5' GAATAGTACCTGGATCCTGATCCC 3'    (SEQ ID NO. 33);
(xxxi)     5' GATATTGGAGGGTTAGGAAGAAGG 3'    (SEQ ID NO. 34);
           5' CTGTACAGTTCAAATTATTGTAACC 3'   (SEQ ID NO. 35);
(xxxii)    5' GACTGATGAAATTATTAGTAAAGAGC 3'  (SEQ ID NO. 36);
           5' CCTCCTTCGTTAGGTGAATCCTC 3'     (SEQ ID NO. 37);
(xxxiii)   5' GGTACTGGATAGATAGTGGAAG 3'      (SEQ ID NO. 57);
           5' CCAGAATCATAAGCTACTGTACC 3'     (SEQ ID NO. 58);
(xxxiv)    5' GTCCCGTATCAGTTCGAGATTCTG 3'    (SEQ ID NO. 40);
           5' CCTCCTTCGTTAGTTGAATCCTC 3'     (SEQ ID NO. 37);
(xxxv)     5' GGGATCAGGATCCAGGTACTATTC 3'    (SEQ ID NO. 43);
           5' GTATCGTTTCTTTCTTCATTCGC 3'     (SEQ ID NO. 44);
(xxxvi)    5' GCTTGGGAGAATAATTTATCAG 3'      (SEQ ID NO. 42);
           5' CCTCCTTCGTTAGTTGAATCCTC 3'     (SEQ ID NO. 37);
(xxxvii)   5' GGACCAAGTTTACCATAATTC 3'       (SEQ ID NO. 45);
           5' GTATCGTTTCTTTCTTCATTCGC 3'     (SEQ ID NO. 44);
```

-continued

| | | |
|---|---|---|
| (xxxviii) | 5' GGAGAATAATTTATCAGTTGGTC 3' | (SEQ ID NO. 46); |
| | 5' GTATCGTTTCTTTCTTCATTCGC 3' | (SEQ ID NO. 44); |
| (xxxix) | 5' CAAGGTATAAGCAGAAGAAAAC 3' | (SEQ ID NO. 47); |
| | 5' CGCACGCCCGGATTCTGTACTATC 3' | (SEQ ID NO. 48); |
| (xl) | 5' ATGTCTCAAATATCCTGGACTCAG 3' | (SEQ ID NO. 49); |
| | 5' CGCACGCCCGGATTCTGTACTATC 3' | (SEQ ID NO. 48); |
| and | | |
| (xli) | 5' GTACTGGATAGATAGTGGAAGTC 3' | (SEQ ID NO. 50); |
| | 5' CACGGCCTTCTTCCTAACCCTCC 3' | (SEQ ID NO. 51). |

10. A method according to claim 7 wherein the primers are selected from the group of primer pairs consisting of:

| | | |
|---|---|---|
| (i) | 5' GGTACTGGATAGATAGTGGA 3' | (SEQ ID NO. 2) |
| | 5' TCGCACGCCCGGATTCTGTA 3' | (SEQ ID NO. 3); |
| (ii) | 5' GAGATTCTGAAATTAATTGG 3' | (SEQ ID NO. 27); |
| | 5' CCTCCTTCGTTAGTTGAATCC 3' | (SEQ ID NO. 59); |
| (iii) | 5' GTTGGCTTATAGATTCTGAGC 3' | (SEQ ID NO. 28); |
| | 5' CAGTTCAAATTATTGTAGCC 3' | (SEQ ID NO. 38); |
| (iv) | 5' GAGATTCTGAAATTAATTGG 3' | (SEQ ID NO. 27); |
| | 5' CAGTTCAAATTATTGTAACC 3' | (SEQ ID NO. 60); |
| (v) | 5' GTTGGCTTATAGATTCTGAGC 3' | (SEQ ID NO. 28); |
| | 5' CCTCCTTCGTTAGTTGAATCC 3' | (SEQ ID NO. 53); |
| (vi) | 5' TAATTGGACATCAAGTTATAAAGC 3' | (SEQ ID NO. 55); |
| | 5' GGAAGATCCAAATAAGAATTATGG 3' | (SEQ ID NO. 56); |
| (vii) | 5' GGTTATTAAGATTCAAATTTCC 3' | (SEQ ID NO. 29); |
| | 5' CGAACTCTGATACGAGCTCCAAGC 3' | (SEQ ID NO. 31); |
| (viii) | 5' TCCCGTATCAGTTCGAGATTCTG 3' | (SEQ ID NO. 30); |
| | 5' CGAACTCTGATACGAGCTCCAAGC 3' | (SEQ ID NO. 31); |
| (ix) | 5' GTTCGAGATTCTGAAATTAATTGG 3' | (SEQ ID NO. 39); |
| | 5' CGAACTCTGATACGAGCTCCAAGC 3' | (SEQ ID NO. 31); |
| (x) | 5' TAATTGGACATCAAGTTATAAAGC 3' | (SEQ ID NO. 53); |
| | 5' CGAACTCTGATACGAGCTCCAAGC 3' | (SEQ ID NO. 31); |
| (xi) | 5' GGTTATTAAGATTCAAATTTCC 3' | (SEQ ID NO. 29); |
| | 5' CGAACTCTGATACGAGCTCCAAGC 3' | (SEQ ID NO. 31); |
| (xii) | 5' TCCCGTATCAGTTCGAGATTCTG 3' | (SEQ ID NO. 30); |
| | 5' GAATAGTACCTGGATCCAGATCCC 3' | (SEQ ID NO. 33); |
| (xiii) | 5' GGGATCAGGATCCAGGTACTATTC 3' | (SEQ ID NO. 53); |
| | 5' GAATAGTACCTGGATCCAGATCCC 3' | (SEQ ID NO. 33); |
| (xiv) | 5' GGTTATTAAGATTCAAATTTCC 3' | (SEQ ID NO. 29); |
| | 5' GAATAGTACCTGGATCCAGATCCC 3' | (SEQ ID NO. 33); |

-continued

| | | |
|---|---|---|
| (xv) | 5' TCCCGTATCAGTTCGAGATTCTG 3' | (SEQ ID NO. 30); |
| | 5' GGAAGATCCAAATAAGAATTATGG 3' | (SEQ ID NO. 56); |
| (xvi) | 5' GTTCGAGATTCTGAAATTAATTGG 3' | (SEQ ID NO. 39); |
| | 5' GGAAGATCCAAATAAGAATTATGG 3' | (SEQ ID NO. 56); |
| (xvii) | 5' GGTTATTAAGATTCAAATTTCC 3' | (SEQ ID NO. 29); |
| | 5' GGAAGATCCAAATAAGAATTATGG 3' | (SEQ ID NO. 56); |
| (xviii) | 5' ATTCGAGATTCTGAAATTAATTGG 3' | (SEQ ID NO. 32); |
| | 5' GAATAGTACCTGGATCCAGATCCC 3' | (SEQ ID NO. 33); |
| (xix) | 5' GATATTGGAGGGTTAGGAAGAAGG 3' | (SEQ ID NO. 34); |
| | 5' CTGTACAGTTCAAATTATTGTAACC 3' | (SEQ ID NO. 35); |
| (xx) | 5' GACTGATGAAATTATTAGTAAAGAGC 3' | (SEQ ID NO. 36); |
| | 5' CCTCCTTCGTTAGGTGAATCCTC 3' | (SEQ ID NO. 37); |
| (xxi) | 5' GGTACTGGATAGATAGTGGAAG 3' | (SEQ ID NO. 57); |
| | 5' CCAGAATCATAAGCTACTGTACC 3' | (SEQ ID NO. 58); |
| (xxii) | 5' GTCCCGTATCAGTTCGAGATTCTG 3' | (SEQ ID NO. 40); |
| | 5' CCTCCTTCGTTAGTTGAATCCTC 3' | (SEQ ID NO. 37); |
| (xxiii) | 5' GGGATCAGGATCCAGGTACTATTC 3' | (SEQ ID NO. 43); |
| | 5' GTATCGTTTCTTTCTTCATTCGC 3' | (SEQ ID NO. 44); |
| (xxiv) | 5' GCTTGGGAGAATAATTTATCAG 3' | (SEQ ID NO. 42); |
| | 5' CCTCCTTCGTTAGTTGAATCCTC 3' | (SEQ ID NO. 37); |
| (xxv) | 5' GGACCAAGTTTACCATAATTC 3' | (SEQ ID NO. 45); |
| | 5' GTATCGTTTCTTTCTTCATTCGC 3' | (SEQ ID NO. 44); |
| (xxvi) | 5' GGAGAATAATTTATCAGTTGGTC 3' | (SEQ ID NO. 46); |
| | 5' GTATCGTTTCTTTCTTCATTCGC 3' | (SEQ ID NO. 44); |
| (xxvii) | 5' CAAGGTATAAGCAGAAGAAAAC 3' | (SEQ ID NO. 47); |
| | 5' CGCACGCCCGGATTCTGTACTATC 3' | (SEQ ID NO. 48); |
| (xxviii) | 5' ATGTCTCAAATATCCTGGACTCAG 3' | (SEQ ID NO. 49); |
| | 5' CGCACGCCCGGATTCTGTACTATC 3' | (SEQ ID NO. 48); |
| and | | |
| (xxix) | 5' GTACTGGATAGATAGTGGAAGTC 3' | (SEQ ID NO. 50); |
| | 5' CACGGCCTTCTTCCTAACCCTCC 3' | (SEQ ID NO. 51). |

11. A method according to claim 7 wherein the primer pair is GGTACTGGATAGATAGTGGA (Forward primer; SEQ ID NO. 2) and TCGCACGCCCGGATTCTGTA Reverse primer; SEQ ID NO. 3 ).

12. A method according to claim 7 wherein the primer pair is GAGATTCTGAAATTAATTGG (Forward primer; SEQ ID NO. 27) and CCTCCTTCGTTAGTTGAATCC (Reverse primer; SEQ ID NO. 59).

13. A method according to claims 2 or 8 wherein the method includes a further step of testing for the viability and or the infectivity of Cryptosporidium organisms in the sample.

14. A kit for the detection of Cryptosporidium isolates: the kit comprising at least a probe or primer(s) selected from the nucleotide sequence defined in claim 1, which is capable of detecting Cryptosporidium isolates.

15. A kit according to claim 14 wherein the kit contains a primer pair selected from the primers defined in claims 9, 10, 11, or 12.

* * * * *

SEQUENCE LISTING

```
(1) GENERAL INFORMATION:

(iii) NUMBER OF SEQUENCES: 68

(2) INFORMATION FOR SEQ ID NO:1:

(i) SEQUENCE CHARACTERISTICS:
          (A) LENGTH: 688 base pairs
```

(B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GATGGTACTG GATAGATAGT GGAAGTCCCG TATCAGTTCG AGATTCTGAA ATTAATTGGA      60

CATCAAGTTA TAAAGCAAGC TGGTTATTAA GATTCAAATT TCCCTTTGAA AAGTGTGGCT     120

TTTTTGATAT TGGAGGGTTA GGAAGAAGGC CGTGTTGGCT TATAGATTCT GAGCTTTCTT     180

GTGCAGTTTG TGGTACAGTA GCTTATGATT CTGGTGGGCT GAATCCCAAT AAATATTCAG     240

AGCTAATTAA GCAGACTGAT GAAATTATTA GTAAAGAGCC AAAGCTTGAT CTTCCAGGTT     300

ACAATAATTT GAACTGTACA GATGCTTGGG AGAATAATTT ATCAGTTGGT CTTTGTCAAA     360

ATGTCTCAAA TATCCTGGAC TCAGCTTGGA GCTCGTATCA GAGTTCGTTA AACTTTCCTA     420

GTATCAACTT TAACTGGAAA GAGGATTCAA CTAACGAAGG AGGGGACCAA GTTTACCATA     480

ATTCTTATTT GGATCTTCCA AGGTATAAGC AGAAGAAAAC ATTTTATTGG GATCAGGATC     540

CAGGTACTAT TCCAGCTTTG TCTGATGAAA TGAAGCTCAT TGGTTTAAGC GCTCAACCAA     600

CATACCATCC TTTGGATAGA AGCTCATCTG GAAGTTTTGA GTCTGATAGT ACAGAATCCG     660

GGCGTGCGAA TGAAGAAAGA AACGATAC                                       688
```

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
GGTACTGGAT AGATAGTGGA                                                  20
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
TCGCACGCCC GGATTCTGTA                                                  20
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
AGTCCCGTAT CAGTTCGAGA                                                  20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

ACTGGATAGA TAGTGGAAGT                                                  20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TTTCTTTCTT CATTCGCACG                                                  20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GTGGAAGTCC CGTATCAGTC                                                  20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ACGCCCGGAT TCTGTACTAT                                                  20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GATAGATAGT GGAAGTCCCG                                                  20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CTGAAATTAA TTGGACATCA                                               20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GTACTATCAG ACTCAAAACT                                               20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GTGGTACTGG ATAGATAGTG                                               20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GTATCGTTTC TTTCTTCATT                                               20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

TGGTACTGGA TAGATAGTGG                                               20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
TATCGTTTCT TTCTTCATTC                                                20
```

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
TAGATAGTGG AAGTCCCGTA                                                20
```

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
TCTTCATTCG CACGCCCGGA                                                20
```

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
ATAGTGGAAG TCCCGTATCA                                                20
```

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
TTTCTTCATT CGCACGCCCG                                                20
```

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
CTGGATAGAT AGTGGAAGTC                                                20
```

(2) INFORMATION FOR SEQ ID NO:21:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:21:

CGTTTCTTTC TTCATTCGCA                                            20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TAATTGGACA TCAAGTATAA                                            20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

TCTGAAATTA ATTGGACATC                                            20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

CTTCCAGATG AGCTTCTATC                                            20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GGTGGTACTG GATAGATAGT                                            20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GGTATCGTTT CTTTCTTCAT                                    20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GAGATTCTGA AATTAATTGG                                    20

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GTTGGCTTAT AGATTCTGAG C                                  21

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GGTTATTAAG ATTCAAATTT CC                                 22

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

TCCCGTATCA GTTCGAGATT CTG                                23

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

CGAACTCTGA TACGAGCTCC AAGC                24

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

ATTCGAGATT CTGAAATTAA TTGG                24

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

GAATAGTACC TGGATCCTGA TCCC                24

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

GATATTGGAG GGTTAGGAAG AAGG                24

(2) INFORMATION FOR SEQ ID NO:35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

CTGTACAGTT CAAATTATTG TAACC               25

(2) INFORMATION FOR SEQ ID NO:36:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

GACTGATGAA ATTATTAGTA AAGAGC              26

(2) INFORMATION FOR SEQ ID NO:37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

CCTCCTTCGT TAGTTGAATC CTC								23

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CAGTTCAAAT TATTGTAGCC								20

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

GTTCGAGATT CTGAAATTAA TTGG							24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

GTCCCGTATC AGTTCGAGAT TCTG							24

(2) INFORMATION FOR SEQ ID NO:41:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

GGAGGGTTAG GAAGAAGGCC GTG							23

(2) INFORMATION FOR SEQ ID NO:42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

GCTTGGGAGA ATAATTTATC AG                       22

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

GGGATCAGGA TCCAGGTACT ATTC                     24

(2) INFORMATION FOR SEQ ID NO:44:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

GTATCGTTTC TTTCTTCATT CGC                      23

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

GGACCAAGTT TACCATAATT C                        21

(2) INFORMATION FOR SEQ ID NO:46:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

GGAGAATAAT TTATCAGTTG GTC                      23

(2) INFORMATION FOR SEQ ID NO:47:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

-continued

CAAGGTATAA GCAGAAGAAA AC							22

(2) INFORMATION FOR SEQ ID NO:48:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

CGCACGCCCG GATTCTGTAC TATC							24

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

ATGTCTCAAA TATCCTGGAC TCAG							24

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

GTACTGGATA GATAGTGGAA GTC							23

(2) INFORMATION FOR SEQ ID NO:51:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

CACGGCCTTC TTCCTAACCC TCC							23

(2) INFORMATION FOR SEQ ID NO:52:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

GGAAGTCCCG TATCAGTTCG AG							22

(2) INFORMATION FOR SEQ ID NO:53:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

CCTCCTTCGT TAGTTGAATC C                                            21

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

CAGTTCAAAT TATTGTAACC                                              20

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

TAATTGGACA TCAAGTTATA AAGC                                         24

(2) INFORMATION FOR SEQ ID NO:56:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

GGAAGATCCA AATAAGAATT ATGG                                         24

(2) INFORMATION FOR SEQ ID NO:57:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

GGTACTGGAT AGATAGTGGA AG                                           22

(2) INFORMATION FOR SEQ ID NO:58:

(i) SEQUENCE CHARACTERISTICS:
        (A) LENGTH: 23 base pairs
        (B) TYPE: nucleic acid
        (C) STRANDEDNESS: single
        (D) TOPOLOGY: linear -continued (ii) MOLECULE TYPE: cDNA (xi) SEQUENCE DESCRIPTION: SEQ ID NO:58:

CCAGAATCAT AAGCTACTGT ACC                                    23

(2) INFORMATION FOR SEQ ID NO:59:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

CCTCCTTCGT TAGTTGAATC C                                      21

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

CAGTTCAAAT TATTGTAACC                                        20

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

GCTTGGTCTG CTCAATGTGG                                        20

(2) INFORMATION FOR SEQ ID NO:62:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

ACAGGGGTGT GGGG                                              14

(2) INFORMATION FOR SEQ ID NO:63:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

| | |
|---|---|
| GACNGGNACN GG | 12 |

(2) INFORMATION FOR SEQ ID NO:64:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

| | |
|---|---|
| CTCTGGGTGT CGTGC | 15 |

(2) INFORMATION FOR SEQ ID NO:65:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

| | |
|---|---|
| GATTTAGGTG ACACTATAG | 19 |

(2) INFORMATION FOR SEQ ID NO:66:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:66:

| | |
|---|---|
| GAAGAAGAAG AAGAA | 15 |

(2) INFORMATION FOR SEQ ID NO:67:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

| | |
|---|---|
| GACAGACAGA CAGACA | 16 |

(2) INFORMATION FOR SEQ ID NO:68:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

| | |
|---|---|
| AGTCGAACCC TGATTCTCCG CCAGG | 25 |